United States Patent
Seitz et al.

(10) Patent No.: US 10,538,795 B2
(45) Date of Patent: Jan. 21, 2020

(54) 5' PROTECTION DEPENDENT AMPLIFICATION

(71) Applicant: Lexogen GmbH, Vienna (AT)

(72) Inventors: Alexander Seitz, Vienna (AT); Irmlind Gabler, Stockerau (AT); Lukas Paul, Vienna (AT)

(73) Assignee: LEXOGEN GMBH, Vienna (AT)

( * ) Notice: Subject to any disclaimer, the term of this patent is extended or adjusted under 35 U.S.C. 154(b) by 27 days.

(21) Appl. No.: 14/414,104

(22) PCT Filed: Jul. 10, 2013

(86) PCT No.: PCT/EP2013/064582
§ 371 (c)(1),
(2) Date: Jan. 10, 2015

(87) PCT Pub. No.: WO2014/009413
PCT Pub. Date: Jan. 16, 2014

(65) Prior Publication Data
US 2015/0147785 A1    May 28, 2015

(30) Foreign Application Priority Data
Jul. 10, 2012    (EP) .................................... 12175694

(51) Int. Cl.
C12P 19/34    (2006.01)
C12Q 1/68    (2018.01)

(52) U.S. Cl.
CPC .................................... C12P 19/34 (2013.01)

(58) Field of Classification Search
None
See application file for complete search history.

(56) References Cited

U.S. PATENT DOCUMENTS

| 5,554,730 A | 9/1996 | Woiszwillo et al. |
| 5,962,271 A * | 10/1999 | Chenchik ............. C12Q 1/6855 435/91.1 |

(Continued)

FOREIGN PATENT DOCUMENTS

| DE | 19920611 | 11/2000 |
| DE | 10105208 | 8/2002 |

(Continued)

OTHER PUBLICATIONS

International Search Report in corresponding International Application PCT/EP2013/064582 dated Apr. 16, 2014.
(Continued)

*Primary Examiner* — Young J Kim
(74) *Attorney, Agent, or Firm* — Nevrivy Patent Law Group P.L.L.C.

(57) ABSTRACT

The present invention relates to methods for generating a labelled nucleic acid from an RNA comprising a 5' protecting group, said method comprises the steps of obtaining a mixture of template strands of nucleic acids, said mixture comprising said RNA and further potentially other nucleic acids without a 5' protecting group, annealing at least one oligonucleotide primer to the template strand of said RNA and potentially other nucleic acids, and template sequence dependent extending said primer, thereby obtaining a complementary nucleic acid strand annealed to its template strand, or providing the RNA in duplex with a complementary nucleic acid strand annealed to its template strand, and optionally modifying the extension product of said nucleic acids without 5' protecting group either on the 5' end of the template strand or on the 3' end of the complementary strand, or both, and labelling a complementary nucleic acid of a double stranded nucleic acid not modified, wherein therefore the labelled nucleic acid did have a 5' protecting group on the RNA template strand, said 5' protecting group (Continued)

Figure 1A:
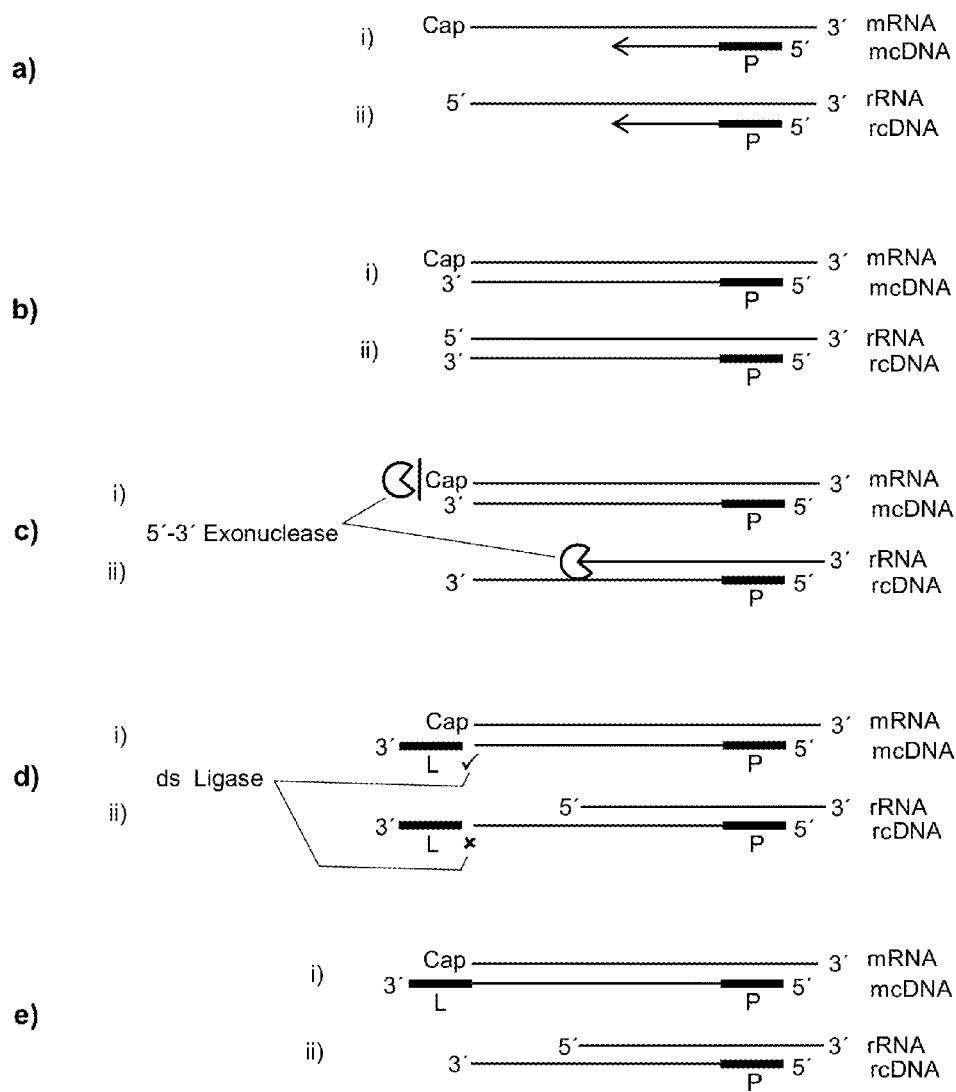

being optionally removed after modification, and/or labelling a complementary nucleic acid of a double strand dependent on the presence of the 5' protecting group on the complementary nucleic acids template RNA strand by double strand dependent ligation, thereby specifically generating a labelled nucleic acid complementary to an RNA at least originally comprising a 5' protecting group.

32 Claims, 6 Drawing Sheets

Specification includes a Sequence Listing.

(56) References Cited

U.S. PATENT DOCUMENTS

| | | | |
|---|---|---|---|
| 5,962,272 | A | 10/1999 | Chenchik et al. |
| 6,022,715 | A | 2/2000 | Merenkova et al. |
| 6,174,669 | B1 | 1/2001 | Hayashizaki et al. |
| 6,558,927 | B1 | 5/2003 | Mueller et al. |
| 8,017,339 | B2 | 9/2011 | Piepenburg et al. |
| 2003/0049637 | A1 | 3/2003 | Park et al. |
| 2004/0220127 | A1 | 11/2004 | Sternberg et al. |
| 2006/0240451 | A1 | 10/2006 | Jendrisak et al. |
| 2008/0108804 | A1 | 5/2008 | Hayashizaki et al. |
| 2009/0311754 | A1 | 12/2009 | Seitz |
| 2010/0159526 | A1* | 6/2010 | Jendrisak ............ C12N 15/1096 435/91.1 |

FOREIGN PATENT DOCUMENTS

| | | |
|---|---|---|
| EP | 0373914 | 6/1990 |
| EP | 2570487 | 3/2013 |
| WO | 2007/062445 | 6/2007 |
| WO | 2007/117039 | 10/2007 |

OTHER PUBLICATIONS

European Search Report in related European Application EP 12175694.4 dated Nov. 21, 2012.
Carninci et al., High-Efficiency Full-Length cDNA Cloning by Biotinylated CAP Trapper, Genomics, vol. 37, pp. 327-336 (1996).
Carninci et al., High Efficiency Selection of Full-length cDNA by Improved Biotinylated Cap Trapper, DNA Research, vol. 4, pp. 61-66 (1997).
Carninci et al., Thermostabilization and thermoactivation of thermolabile enzymes by trehalose and its application for the synthesis of full length cDNA, Proc. Natl. Acad. Sci., vol. 95, pp. 520-524 (Jan. 1998).
Cloonan et al., Stem cell transcriptome profiling via massive-scale mRNA sequencing, Nature Methods, vol. 5, No. 7, pp. 613-619 (Jul. 2008).
Edery et al., An Efficient Strategy to Isolate Full-Length cDNAs Based on an mRNA Cap Retention Procedure (CAPture), Molecular and Cellular Biology, vol. 15, No. 6, pp. 3363-3371 (Jun. 1995).
Efimov et al., Detection of the 5'-cap structure of messenger RNAs with the use of the cap-jumping approach, Nucleic Acids Research, vol. 29, No. 22, pp. 4751-4759 (2001).
Furuichi et al., A blocked structure at the 5' terminus of mRNA from cytoplasmic polyhedrosis virus, Nature, vol. 253, pp. 374-375 (Jan. 1975).
Invitrogen Life Technologies Instruction Manual, GeneRacer Kit for full-length, RNA ligase-mediated rapid amplification of 5' and 3' cDNA ends (RLM-RACE), Invitrogen Corporation, Version L, pp. 1-52 (Apr. 8, 2004).
Lau et al., An Abundant Class of Tiny RNAs with Probable Regulatory Roles in Caenorhabditis elegans, Science, vol. 294, pp. 858-862 (Oct. 2001).
Maruyama et al., Oligo-capping: a simple method to replace the cap structure of eukaryotic mRNAs with oligoribonucleotides, Gene, vol. 138, pp. 171-174 (1994).
Schmidt and Mueller, CapSelect: A highly sensitive method for 5' CAP-dependent enrichment of full-length cDNA in PCR-mediated analysis of mRNAs, Nucleic Acids Research, vol. 27, No. 21, e31, pp. i-iv (1999).
Spiess and Ivell, A Highly Efficient Method for Long-Chain cDNA Synthesis Using Trehalose and Betaine, Analytical Biochemistry, vol. 301, pp. 168-174 (2002).
Suzuki et al., Construction and characterization of a full length-enriched and a 5'-end-enriched cDNA library, Gene, vol. 200, pp. 149-156 (1997).
Written Opinion of the International Searching Authority for corresponding International Application PCT/EP2013/064582 dated Jan. 10, 2015.
Chinese Office Action for Chinese Patent Application No. 201380036635.0, dated Dec. 28, 2015.
English translation of Chinese Office Action for Chinese Patent Application No. 201380036635.0, dated Dec. 28, 2015.
Kato et al., Vector-Capping: A Simple Method for Preparing a High-Quality Full-Length cDNA Library, DNA Research, vol. 12, pp. 53-62 (2005).
Office Action from Chinese Appl. No. 201380036635.0, dated Sep. 18, 2016.
English language translation of Office Action from Chinese Appl. No. 201380036635.0, dated Sep. 18, 2016.
Cecilia et al., "Full-length-enriched cDNA libraries from Echinococcus granulosus contain separate populations of oligo capped and trans-spliced transcripts and a high evel of predicted signal peptide sequences," Molecular & Biochemical Parasitology, 122:171-180 (2002).
Kato et al., "Vector-Capping: A Simple Method for Preparing a High-Quality Full-Length cDNA Library," DNA Research 12:53-62 (2005).

* cited by examiner

SEQUENCE LISTING

```
<160> NUMBER OF SEQ ID NOS: 48

<210> SEQ ID NO 1
<211> LENGTH: 22
<212> TYPE: DNA
<213> ORGANISM: Artificial
<220> FEATURE:
<223> OTHER INFORMATION: template nucleotide

<400> SEQUENCE: 1
```

```
gctaatacga ctcactatag tt                                              22
```

<210> SEQ ID NO 2
<211> LENGTH: 52
<212> TYPE: DNA
<213> ORGANISM: Artificial
<220> FEATURE:
<223> OTHER INFORMATION: template nucleotide
<220> FEATURE:
<221> NAME/KEY: misc_feature
<222> LOCATION: (1)..(1)
<223> OTHER INFORMATION: ribonucleotide

<400> SEQUENCE: 2

```
aagcctatct atatgttctt gacaggtgac aactatagtg agtcgtatta gc             52
```

<210> SEQ ID NO 3
<211> LENGTH: 33
<212> TYPE: RNA
<213> ORGANISM: Artificial
<220> FEATURE:
<223> OTHER INFORMATION: template nucleotide
<220> FEATURE:
<221> NAME/KEY: misc_feature
<222> LOCATION: (1)..(1)
<223> OTHER INFORMATION: 5' triphosphate

<400> SEQUENCE: 3

```
guugucaccu gucaagaaca uauagauagg cuu                                  33
```

<210> SEQ ID NO 4
<211> LENGTH: 33
<212> TYPE: RNA
<213> ORGANISM: Artificial
<220> FEATURE:
<223> OTHER INFORMATION: template nucleotide
<220> FEATURE:
<221> NAME/KEY: misc_feature
<222> LOCATION: (1)..(1)
<223> OTHER INFORMATION: 5' m7Gppp (cap structure)

<400> SEQUENCE: 4

```
guugucaccu gucaagaaca uauagauagg cuu                                  33
```

<210> SEQ ID NO 5
<211> LENGTH: 33
<212> TYPE: RNA
<213> ORGANISM: Artificial
<220> FEATURE:
<223> OTHER INFORMATION: template nucleotide
<220> FEATURE:
<221> NAME/KEY: misc_feature
<222> LOCATION: (1)..(1)
<223> OTHER INFORMATION: 5' m7Gppp[m2'-O] (methylated cap structure)

<400> SEQUENCE: 5

```
guugucaccu gucaagaaca uauagauagg cuu                                  33
```

<210> SEQ ID NO 6
<211> LENGTH: 46
<212> TYPE: DNA
<213> ORGANISM: Artificial
<220> FEATURE:
<223> OTHER INFORMATION: RT primer

<400> SEQUENCE: 6

```
ttcgaccttc agattagcaa cggagcctat ctatatgttc ttgaca                    46
```

```
<210> SEQ ID NO 7
<211> LENGTH: 32
<212> TYPE: RNA
<213> ORGANISM: Artificial
<220> FEATURE:
<223> OTHER INFORMATION: template
<220> FEATURE:
<221> NAME/KEY: misc_feature
<222> LOCATION: (1)..(1)
<223> OTHER INFORMATION: 5' monophosphate

<400> SEQUENCE: 7
guugucaccu gucaagaaca uauagauagg cu                                32

<210> SEQ ID NO 8
<211> LENGTH: 32
<212> TYPE: RNA
<213> ORGANISM: Artificial
<220> FEATURE:
<223> OTHER INFORMATION: template

<400> SEQUENCE: 8
guugucaccu gucaagaaca uauagauagg cu                                32

<210> SEQ ID NO 9
<211> LENGTH: 55
<212> TYPE: DNA
<213> ORGANISM: Artificial
<220> FEATURE:
<223> OTHER INFORMATION: cDNA

<400> SEQUENCE: 9
ttcgaccttc agattagcaa cggagcctat ctatatgttc ttgacaggtg acaac       55

<210> SEQ ID NO 10
<211> LENGTH: 27
<212> TYPE: DNA
<213> ORGANISM: Artificial
<220> FEATURE:
<223> OTHER INFORMATION: linker
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (27)..(27)
<223> OTHER INFORMATION: dideoxynucleotide

<400> SEQUENCE: 10
tatagtgagt cgtattacat atcaatc                                      27

<210> SEQ ID NO 11
<211> LENGTH: 28
<212> TYPE: DNA
<213> ORGANISM: Artificial
<220> FEATURE:
<223> OTHER INFORMATION: adenylated linker
<220> FEATURE:
<221> NAME/KEY: misc_feature
<222> LOCATION: (1)..(1)
<223> OTHER INFORMATION: adenylation (ppA)
<220> FEATURE:
<221> NAME/KEY: misc_feature
<222> LOCATION: (28)..(28)
<223> OTHER INFORMATION: dideoxynucleotide

<400> SEQUENCE: 11
atatagtgag tcgtattaca tatcaatc                                     28
```

```
<210> SEQ ID NO 12
<211> LENGTH: 26
<212> TYPE: DNA
<213> ORGANISM: Artificial
<220> FEATURE:
<223> OTHER INFORMATION: double stranded part for adaptor
<220> FEATURE:
<221> NAME/KEY: misc_feature
<222> LOCATION: (1)..(1)
<223> OTHER INFORMATION: C3 spacer modification

<400> SEQUENCE: 12
attgatatgt aatacgactc actata                                          26

<210> SEQ ID NO 13
<211> LENGTH: 81
<212> TYPE: DNA
<213> ORGANISM: Artificial
<220> FEATURE:
<223> OTHER INFORMATION: ligated cDNA

<400> SEQUENCE: 13
ttcgaccttc agattagcaa cggagcctat ctatatgttc ttgacaggtg acaactatag     60
tgagtcgtat tacatatcaa t                                               81

<210> SEQ ID NO 14
<211> LENGTH: 59
<212> TYPE: DNA
<213> ORGANISM: Artificial
<220> FEATURE:
<223> OTHER INFORMATION: ligation to 3' OH or RNA
<220> FEATURE:
<221> NAME/KEY: misc_feature
<222> LOCATION: (1)..(1)
<223> OTHER INFORMATION: 5' triphosphate
<220> FEATURE:
<221> NAME/KEY: misc_feature
<222> LOCATION: (59)..(59)
<223> OTHER INFORMATION: dideoxynucleotide

<400> SEQUENCE: 14
guugucaccu gucaagaaca uauagauagg cutatagtga gtcgtattac atatcaatc     59

<210> SEQ ID NO 15
<211> LENGTH: 23
<212> TYPE: DNA
<213> ORGANISM: Artificial
<220> FEATURE:
<223> OTHER INFORMATION: RT primer

<400> SEQUENCE: 15 ggcgttttttt tttttttttt ttv                                            23

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
ttattgatat gtaatacgac tcactat                                         27

<210> SEQ ID NO 17
<211> LENGTH: 23
<212> TYPE: DNA
<213> ORGANISM: Artificial
```

```
<220> FEATURE:
<223> OTHER INFORMATION: primer

<400> SEQUENCE: 17
ggcgtttttt ttttttttt tta                                        23

<210> SEQ ID NO 18
<211> LENGTH: 18
<212> TYPE: DNA
<213> ORGANISM: Artificial
<220> FEATURE:
<223> OTHER INFORMATION: random nonamer primer with overhang
<220> FEATURE:
<221> NAME/KEY: misc_feature
<222> LOCATION: (1)..(1)
<223> OTHER INFORMATION: 5' Amino C12 spacer
<220> FEATURE:
<221> NAME/KEY: misc_feature
<222> LOCATION: (10)..(18)
<223> OTHER INFORMATION: n is a, c, g, or t

<400> SEQUENCE: 18
tctcaggcgn nnnnnnnn                                             18

<210> SEQ ID NO 19
<211> LENGTH: 25
<212> TYPE: DNA
<213> ORGANISM: Artificial
<220> FEATURE:
<223> OTHER INFORMATION: primer

<400> SEQUENCE: 19
tagaattacc acagttatcc aagta                                     25

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
gtacttcagg gtcaggatac ct                                        22

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
tatctgacat ctctacttta ggaatt                                    26

<210> SEQ ID NO 22
<211> LENGTH: 61
<212> TYPE: DNA
<213> ORGANISM: Artificial
<220> FEATURE:
<223> OTHER INFORMATION: complementary nucleic acid
<220> FEATURE:
<221> NAME/KEY: misc_feature
<222> LOCATION: (1)..(1)
<223> OTHER INFORMATION: 5' C12 Spacer

<400> SEQUENCE: 22
agtctaatcg ttgaatggcc gtcgttttga gcctatctat atgttcttga caggtgacaa    60
``` c                                                                61

<210> SEQ ID NO 23
<211> LENGTH: 62
<212> TYPE: DNA
<213> ORGANISM: Artificial
<220> FEATURE:
<223> OTHER INFORMATION: complementary nucleic acid
<220> FEATURE:
<221> NAME/KEY: misc_feature
<222> LOCATION: (1)..(1)
<223> OTHER INFORMATION: 5' C12 Spacer

<400> SEQUENCE: 23
agtctaatcg ttgaatggcc gtcgttttga gcctatctat atgttcttga caggtgacaa      60
cc                                                                    62

<210> SEQ ID NO 24
<211> LENGTH: 63
<212> TYPE: DNA
<213> ORGANISM: Artificial
<220> FEATURE:
<223> OTHER INFORMATION: complementary nucleic acid
<220> FEATURE:
<221> NAME/KEY: misc_feature
<222> LOCATION: (1)..(1)
<223> OTHER INFORMATION: 5' C12 Spacer

<400> SEQUENCE: 24
agtctaatcg ttgaatggcc gtcgttttga gcctatctat atgttcttga caggtgacaa      60
ccc                                                                   63

<210> SEQ ID NO 25
<211> LENGTH: 64
<212> TYPE: DNA
<213> ORGANISM: Artificial
<220> FEATURE:
<223> OTHER INFORMATION: complementary nucleic acid
<220> FEATURE:
<221> NAME/KEY: misc_feature
<222> LOCATION: (1)..(1)
<223> OTHER INFORMATION: 5' C12 Spacer

<400> SEQUENCE: 25
agtctaatcg ttgaatggcc gtcgttttga gcctatctat atgttcttga caggtgacaa      60
cccc                                                                  64

<210> SEQ ID NO 26
<211> LENGTH: 67
<212> TYPE: DNA
<213> ORGANISM: Artificial
<220> FEATURE:
<223> OTHER INFORMATION: complementary nucleic acid
<220> FEATURE:
<221> NAME/KEY: misc_feature
<222> LOCATION: (1)..(1)
<223> OTHER INFORMATION: 5' C12 Spacer

<400> SEQUENCE: 26
agtctaatcg ttgaatggcc gtcgttttga gcctatctat atgttcttga caggtgacaa      60
ccccccc                                                               67

<210> SEQ ID NO 27
<211> LENGTH: 88
<212> TYPE: DNA
<213> ORGANISM: Artificial

```
<220> FEATURE:
<223> OTHER INFORMATION: cDNA
<220> FEATURE:
<221> NAME/KEY: misc_feature
<222> LOCATION: (1)..(1)
<223> OTHER INFORMATION: 5' C12 Spacer
<220> FEATURE:
<221> NAME/KEY: misc_feature
<222> LOCATION: (88)..(88)
<223> OTHER INFORMATION: dideoxynucleotide

<400> SEQUENCE: 27
agtctaatcg ttgaatggcc gtcgttttga gcctatctat atgttcttga caggtgacaa    60
ctatagtgag tcgtattaca tatcaatc                                       88

<210> SEQ ID NO 28
<211> LENGTH: 89
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (1)..(1)
<223> OTHER INFORMATION: 5' C12 Spacer
<220> FEATURE:
<221> NAME/KEY: misc_feature
<222> LOCATION: (89)..(89)
<223> OTHER INFORMATION: dideoxynucleotide

<400> SEQUENCE: 28
agtctaatcg ttgaatggcc gtcgttttga gcctatctat atgttcttga caggtgacaa    60
cctatagtga gtcgtattac atatcaatc                                      89

<210> SEQ ID NO 29
<211> LENGTH: 247
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (219)..(219)
<223> OTHER INFORMATION: n is a, c, g, or t

<400> SEQUENCE: 29
ttcatgtgag gcgggtggaa ctgtgttacg tagcagttca gtatgttcgg cttcccattc    60
tccggtgggt ggcgtgagta tacttgaatt tgaggggttt tctggatagc atacaggccg   120
gtcagtgaga caagcaccag aaagaccagg gtcaccgagc gagccatgct gacgactgaa   180
gcgaccgcga ctgaagcgcc gagtagcagc cactgaaant atagtgagtc gtattacata   240
tcaataa                                                              247

<210> SEQ ID NO 30
<211> LENGTH: 60
<212> TYPE: DNA
<213> ORGANISM: Artificial
<220> FEATURE:
<223> OTHER INFORMATION: RNA - linker ligation product
<220> FEATURE:
<221> NAME/KEY: misc_feature
<222> LOCATION: (1)..(1)
<223> OTHER INFORMATION: 5' cap - (m7Gppp)
<220> FEATURE:
<221> NAME/KEY: misc_feature
<222> LOCATION: (60)..(60)
<223> OTHER INFORMATION: dideoxynucleotide
```

```
<400> SEQUENCE: 30
guugucaccu gucaagaaca uauagauagg cuuuauagug agucguauua cauaucaauc    60

<210> SEQ ID NO 31
<211> LENGTH: 60
<212> TYPE: DNA
<213> ORGANISM: Artificial
<220> FEATURE:
<223> OTHER INFORMATION: ligation product
<220> FEATURE:
<221> NAME/KEY: misc_feature
<222> LOCATION: (1)..(1)
<223> OTHER INFORMATION: 5' cap - m7Gppp[m2'-O]
<220> FEATURE:
<221> NAME/KEY: misc_feature
<222> LOCATION: (60)..(60)
<223> OTHER INFORMATION: dideoxynucleotide

<400> SEQUENCE: 31
guugucaccu gucaagaaca uauagauagg cuuuauagug agucguauua cauaucaauc    60

<210> SEQ ID NO 32
<211> LENGTH: 60
<212> TYPE: DNA
<213> ORGANISM: Artificial
<220> FEATURE:
<223> OTHER INFORMATION: ligation product
<220> FEATURE:
<221> NAME/KEY: misc_feature
<222> LOCATION: (1)..(1)
<223> OTHER INFORMATION: 5' triphosphate
<220> FEATURE:
<221> NAME/KEY: misc_feature
<222> LOCATION: (60)..(60)
<223> OTHER INFORMATION: dideoxynucleotide

<400> SEQUENCE: 32
guugucaccu gucaagaaca uauagauagg cuuuauagug agucguauua cauaucaauc    60

<210> SEQ ID NO 33
<211> LENGTH: 28
<212> TYPE: DNA
<213> ORGANISM: Artificial
<220> FEATURE:
<223> OTHER INFORMATION: non-template nucleotide addition product
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (28)..(28)
<223> OTHER INFORMATION: dideoxynucleotide (c)

<400> SEQUENCE: 33
ctatagtgag tcgtattaca tatcaatc                                       28

<210> SEQ ID NO 34
<211> LENGTH: 28
<212> TYPE: DNA
<213> ORGANISM: Artificial
<220> FEATURE:
<223> OTHER INFORMATION: non-template nucleotide addition product
<220> FEATURE:
<221> NAME/KEY: misc_feature
<222> LOCATION: (1)..(1)
<223> OTHER INFORMATION: 5' adenylation (ppA modification)
<220> FEATURE:
<221> NAME/KEY: misc_feature
<222> LOCATION: (28)..(28)
<223> OTHER INFORMATION: dideoxynucleotide (c)
```

```
<400> SEQUENCE: 34
ctatagtgag tcgtattaca tatcaatc                                          28

<210> SEQ ID NO 35
<211> LENGTH: 30
<212> TYPE: DNA
<213> ORGANISM: Artificial
<220> FEATURE:
<223> OTHER INFORMATION: non-template nucleotide addition product
<220> FEATURE:
<221> NAME/KEY: misc_feature
<222> LOCATION: (1)..(1)
<223> OTHER INFORMATION: 5' Biotin modification
<220> FEATURE:
<221> NAME/KEY: misc_feature
<222> LOCATION: (30)..(30)
<223> OTHER INFORMATION: deoxyA

<400> SEQUENCE: 35
ttggattgat atgtaatacg actcactata                                        30

<210> SEQ ID NO 36
<211> LENGTH: 22
<212> TYPE: DNA
<213> ORGANISM: Artificial
<220> FEATURE:
<223> OTHER INFORMATION: non-template nucleotide addition product

<400> SEQUENCE: 36
tatgttcttg acaggtgaca ac                                                22

<210> SEQ ID NO 37
<211> LENGTH: 23
<212> TYPE: DNA
<213> ORGANISM: Artificial
<220> FEATURE:
<223> OTHER INFORMATION: non-template nucleotide addition product

<400> SEQUENCE: 37
tatgttcttg acaggtgaca acc                                               23

<210> SEQ ID NO 38
<211> LENGTH: 24
<212> TYPE: DNA
<213> ORGANISM: Artificial
<220> FEATURE:
<223> OTHER INFORMATION: non-template nucleotide addition product

<400> SEQUENCE: 38
tatgttcttg acaggtgaca accc                                              24

<210> SEQ ID NO 39
<211> LENGTH: 25
<212> TYPE: DNA
<213> ORGANISM: Artificial
<220> FEATURE:
<223> OTHER INFORMATION: ligation product

<400> SEQUENCE: 39
tatgttcttg acaggtgaca acccc                                             25

<210> SEQ ID NO 40
<211> LENGTH: 25
<212> TYPE: DNA
<213> ORGANISM: Artificial
<220> FEATURE:
```

<223> OTHER INFORMATION: 5'PTO protected oligo dT primer

<400> SEQUENCE: 40
tatgttcttg acaggtgaca acccc                                                 25

<210> SEQ ID NO 41
<211> LENGTH: 26
<212> TYPE: DNA
<213> ORGANISM: Artificial
<220> FEATURE:
<223> OTHER INFORMATION: 3? primer

<400> SEQUENCE: 41
tatgttcttg acaggtgaca accccc                                                26

<210> SEQ ID NO 42
<211> LENGTH: 50
<212> TYPE: DNA
<213> ORGANISM: Artificial
<220> FEATURE:
<223> OTHER INFORMATION: 5' primer
<220> FEATURE:
<221> NAME/KEY: misc_feature
<222> LOCATION: (50)..(50)
<223> OTHER INFORMATION: dideoxynucleotide (c)

<400> SEQUENCE: 42
tatgttcttg acaggtgaca acctatagtg agtcgtatta catatcaatc                      50

<210> SEQ ID NO 43
<211> LENGTH: 28
<212> TYPE: DNA
<213> ORGANISM: Artificial
<220> FEATURE:
<223> OTHER INFORMATION: primer

<400> SEQUENCE: 43
tctcaggcgt tttttttttt tttttttv                                              28

<210> SEQ ID NO 44
<211> LENGTH: 27
<212> TYPE: DNA
<213> ORGANISM: Artificial
<220> FEATURE:
<223> OTHER INFORMATION: primer

<400> SEQUENCE: 44
tctcaggcgt tttttttttt tttttt                                                27

<210> SEQ ID NO 45
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(1)
<223> OTHER INFORMATION: 5' Biotin modification

<400> SEQUENCE: 45
ttggattgat atgtaatacg actcactata                                            30

<210> SEQ ID NO 46
<211> LENGTH: 24
<212> TYPE: DNA
<213> ORGANISM: Artificial

```
<220> FEATURE:
<223> OTHER INFORMATION: primer

<400> SEQUENCE: 46
catatgcttg tctcaaagat taag                                              24

<210> SEQ ID NO 47
<211> LENGTH: 28
<212> TYPE: DNA
<213> ORGANISM: Artificial
<220> FEATURE:
<223> OTHER INFORMATION: primer

<400> SEQUENCE: 47
cagtttctaa tatgctatac aatttatg                                          28

<210> SEQ ID NO 48
<211> LENGTH: 28
<212> TYPE: DNA
<213> ORGANISM: Artificial
<220> FEATURE:
<223> OTHER INFORMATION: primer

<400> SEQUENCE: 48
tatttaaagt aagatataaa gaaggtga                                          28
```

5' PROTECTION DEPENDENT AMPLIFICATION

REFERENCE TO A SEQUENCE LISTING SUBMITTED ELECTRONICALLY VIA EFS-WEB

The content of the sequence listing (Name: Sequence_Listing_ST25.txt, Size: 12,612 bytes; and Date of Creation: Jan. 10, 2015) electronically submitted via EFS-Web is incorporated by reference in its entirety.

FIELD OF INVENTION

The present invention relates to the field of analyzing complex mixtures of nucleic acids, especially the analysis of and selection for nucleic acids that provide for different nucleotides at their 5' region, in particular for the purification of RNA, especially capped RNA such as messenger RNA (mRNA), and enrichment of cDNA copies derived from such RNA.

BACKGROUND

Nucleic acids can provide for different chemical structures on their 5' end, such as is the case for e.g. a total RNA extract. For instance 28S and 18S ribosomal RNA (rRNA) as well as microRNA (miRNA) and 5' degraded RNAs have a 5' monophosphate. Other RNAs have a 5' diphosphate such as 5S rRNA intermediates or a 5' OH such as 18S rRNA intermediates and transfer RNA (tRNA) intermediates. Prokaryotic mRNAs have a 5' triphosphate and eukaryotic mRNAs have a cap structure (1). The cap structure is in its essence a guanosine that is methylated on the N7 of the purine ring and linked on its 5' position to the 5' position of the next nucleotide of the RNA through a triphosphate bridge.

As different chemical structures on the 5' position of the RNAs 5' nucleotide provide information about the RNAs function and pathway of synthesis and degradation, methods that select for RNA with different 5' ends are important tools for the analysis of RNA.

Furthermore, for many downstream analyses the RNA is reverse transcribed into cDNA as many powerful methods such as PCR exist for DNA analysis. Therefore it is most desirable that the information of the identity of specific 5' RNA ends is transferred to the cDNA and at the same time the cDNA is as faithfully a copy of the RNA as possible. This is of special importance in the full length analysis of RNA molecules as only the full length RNA molecule reveals the entire sequence identity of an RNA.

Several methods exist that can select for different classes of RNA. For instance, eukaryotic mRNA is often selected based on the cap structure and/or a 3' poly A tail. Enrichment processes that target the poly A tail, such as oligo dT column chromatography, are well known in the art. Oligo dT priming during first strand cDNA synthesis is another process to copy mRNAs during reverse transcription. However, methods that select for the poly A tail do not select against 5' degraded or fragmented mRNA, and certain RNA classes that are not polyadenylated, such as histone mRNA.

Therefore also methods have been developed that use the presence of the cap structure to purify or enrich for mRNA or its cDNA.

For instance, oligo capping (2-4) is one method used to add an oligonucleotide to the 5' end of the mRNA. It is a multistep protocol that requires the RNA sample to be dephosphorylated leaving only 5' OH and cap structures. The cap is then cleaved off by tobacco acid phosphatase (TAP) leaving a 5' monophosphate that can then be used in a subsequent reaction to ligate an oligonucleotide to this 5' monophosphate. In essence this oligonucleotide provides for a sequence tag that can be selected for, e.g. after reverse transcription, by PCR amplification. Using the oligo capping method in conjunction with selection for full length amplification products (e.g. as described in WO 2007/062445) the present inventors have found that oligo capping introduces considerable bias towards shorter RNA molecules, due to the multiple enzymatic steps utilized that degrade long RNA molecules. Thus, methods are desirable that conserve the RNA or its full length sequence information during amplification and cap structure selection.

The cap trapper method (5;6) is another method that selects for mRNAs sequences by first biotinylating the cap, and then reverse transcribing the RNA. In a further step RNAse I is used to hydrolyze all RNA that is not in a hybrid with the cDNA. Then the mRNA/cDNA hybrids are bound to magnetic avidin beads, effectively selecting for full length cDNA copies that are then further processed.

A similar method is CAPture (7) and EP 373 914 A2 that uses a cap binding protein (eukaryotic initiation factor 4) coupled to a solid support to select for mRNA/cDNA hybrids in conjunction with an RNAse I digestion step.

Efimov et al. (8) and U.S. Pat. No. 6,022,715 provide for a method of chemically ligating an oligonucleotide to the cap of an RNA in a multistep procedure.

Other methods use the property of the reverse transcriptase to add 1-6 cytosines (Cs) to the cDNA strand when reaching the cap to select for these Cs. For instance, the CapSelect (9) ligates an adapter, depending to the presence of 3-4 Cs to the cDNA, to enrich during amplification for such tailed cDNA.

In U.S. Pat. Nos. 5,962,271 and 5,962,272 a method is disclosed that adds a defined sequence to the 3' end of the cDNA based on the template switching ability of the reverse transcriptase, that can be complemented with the cap dependent C addition to enrich for full length cDNA. For both the Template Switch and the Tailing (CapSelect), the addition of Cs was presumed to be favored if a Cap is present (9). However, others have found that addition also takes place if no Cap is present (10), making these methods not very selective. In addition, when the reverse transcriptase is stopped at secondary or tertiary RNA structures during reverse transcription, again a template switch can occur providing for a spurious tag.

In US 2010/159526 A1 methods are disclosed that add a tagging oligonucleotide to 5' triphosphates of prokaryotic mRNA by first incubating the RNA with a polyphosphatase to reduce the 5' triphosphate to a 5' monophosphate that then can act as a donor to accept a 3' OH of a tagging oligonucleotide in a subsequent ligation reaction. Again the selection for the prokaryotic mRNA is carried out before cDNA synthesis.

WO 2007/117039 A1 and US 2008/0108804 A1 describe a method wherein mRNA is selected by removing a cap and ligating a nucleic acid molecule to the residual phosphate left by cap removal. To distinguish mRNA from other RNA, non-capped RNA molecules are previously dephosphorylated to prevent ligation thereto. Modified RNA is then transcribed to cDNA.

U.S. Pat. Nos. 6,174,669 and 6,022,715 relate to a further cap modification method wherein the diol structure in the 5'cap is oxidized to form a reactive dialdehyde that is further labeled with a tag. However, oxidation is hazardous to RNA durability and RNA may be degraded.

DE 199 20 611 A1 and US 2003/0049637 A1 describe modifying a cDNA by ligating an adapter for complementary strand synthesis. The adaptor is attached by first synthesizing several Cs by using high Mg and Mn-Ion concentrations during RT and ligating a short oligonucleotide with a terminal transferase.

In DE 101 05 208 A1 it is disclosed that RT efficiency can be increased by including betaine to the RT reaction during cDNA synthesis.

In summary, methods used to date are therefore either not very selective or multistep protocols. As especially RNA is instable, multistep protocols increase the chance of RNA to be fragmented. The use of multiple enzymatic reactions, that very often require divalent cations such as $Mg^{2+}$ and elevated temperatures, per se leads to RNA degradation. In addition, enzyme preparations are never truly pure and even minor amounts of nucleases increase the chance of RNA degradation. Finally, each additional reaction step also increases the chance that an RNase contamination is introduced that would degrade the RNA.

As longer RNA molecules are at increased risk of degradation than shorter RNA molecules, also a bias towards shorter RNA molecules is introduced. Therefore methods that increase selectivity and sensitivity in tagging specific 5' ends of a transcript while at the same time offering the possibility to test for the full length sequence information of the RNA are needed.

SUMMARY OF THE INVENTION

The present invention provides a method for generating a labelled nucleic acid from an RNA comprising a 5' protecting group, such as a 5' cap and/or 5' polyphosphate structure, said method comprises the steps of:
a) obtaining a mixture of template strands of nucleic acids, said mixture comprising said RNA and further potentially other nucleic acids without a 5' protecting group, and
b1) annealing at least one oligonucleotide primer to the template strand of said RNA and potentially other nucleic acids, and template sequence dependent extending said primer, thereby obtaining a complementary nucleic acid strand annealed to its template strand, or b2) providing the RNA in duplex with a complementary nucleic acid strand annealed to its template strand, and
c) optionally modifying the extension product of said nucleic acids without and/or with the 5' protecting group either on the 5' end of the template strand or on the 3' end of the complementary strand, or both, and
d) labelling a complementary nucleic acid of the RNA, thereby specifically generating a labelled nucleic acid complementary to an RNA at least originally comprising a 5' protecting group. Step d1 can be distinguished by (combinable) options d1) labelling a complementary nucleic acid of a double stranded nucleic acid not modified in step c) and/or d2) labelling a complementary nucleic acid of a double strand dependent on the presence of the 5' protecting group on the complementary nucleic acids template RNA strand by double strand dependent ligation. The individual step allow several options, most of them following the principle that the 3' OH on the complementary strand near the 5' terminus of the template is not accessible as in case of the duplexes without the protecting group. In case of a 5' protecting group being present in the duplex, the 3' OH remains accessible on the complementary strand. Accessibility can be used for labeling.

The steps are performed in this order from a) to d), with steps b) and d) comprising alternatives that can be combined with each other. E.g. step d2) can be seen as a modification according to step c) combinable with further labelling d1). However, step d2) is also fulfilling the objective alone, without a modification on the nucleic acids without the 5' protecting group (the undesired byproducts in the nucleic acid sample, that shall not be labelled).

The present invention is further defined in the claims.

DETAILED DISCLOSURE OF THE INVENTION

The present invention relates to methods where in essence an RNA is first reverse transcribed into a complementary nucleic acid, such as a cDNA, before any potentially harmful steps, such as oxidation or multi-enzyme exposure, are practiced on the RNA. Thereby the full-length information of the RNA is preserved in the complementary nucleic acid. This is particularly beneficial in preserving long RNA sequences.

5' protecting group are common in natural mRNA species and protect against digestion by 5'-3' exonucleases. Examples of 5' protecting group are 5' cap structures that are common in eukaryotes and 5' triphosphates that are common in prokaryotes. The present invention can be performed with both of these protection groups. Indeed any protecting group on the 5' end can be used. Examples are 5' polyphosphates in general, including 5' diphosphates and 5' triphosphates. A "polyphosphate" is understood as a phosphate ester with at least two phosphate groups, e.g. 2, 3, 4, 5 or more phosphates, that are preferably joined consecutively by ester bonds. Of course any other natural or non-natural protecting group can be used that protects against digestion by 5'-3' exonucleases, however preferred are 5' cap structures or 5' polyphosphates, especially 5' triphosphates. A nucleic acid with the 5' protecting group is referred to as "protected" nucleic acid herein. A nucleic acid without the 5' protecting group is referred to as "non-protected" nucleic acid herein.

In preferred embodiments the complementary nucleic acid is DNA, but in other embodiments it may also be RNA or a DNA/RNA copolymer.

In further preferred embodiments the template nucleic acid is RNA—both, the nucleic acids of interest with the protecting group and the non-protected nucleic acids that are modified. Both are provided in the mixture in step a).

Alternatively, to perform the nucleic acid synthesis on spot (step b1), it is also possible to provide a duplex nucleic acid with the RNA (step b2). E.g. a cDNA::RNA or RNA::RNA hybrid is provided. All further steps can be combined with any one of these alternatives as they relate to the same inventive concept.

Subsequently an optional reaction c) is carried out that will inactivate all 3' end sequences of complementary nucleic acids, e.g. cDNAs, that are not in a hybrid with a specific 5' end of an RNA of interest, e.g. having the protecting group like the Cap structure, so that d1) a linker sequence or other label can only be added in a double strand specific manner to those 3' ends of the complementary nucleic acids that are still available for labelling (are "active"). In step d1) a complementary nucleic acid of a double stranded nucleic acid not modified in step c) is labelled, wherein therefore the labelled nucleic acid did have a 5' protecting group on the RNA template strand in step c), said 5' protecting group being optionally removed after performing step c) (and possibly before step d1)).

In an embodiment without modification of the non-protected nucleic acid (step c)), also step d2 can be performed.

Of course also d2) can be combined with this step c), but it is not essential. In embodiment d2), a complementary nucleic acid of a double strand is labelled dependent on the presence of the 5' protecting group on the complementary nucleic acids template RNA strand by double strand dependent ligation.

In a preferred embodiment the reaction of step d2) is carried out by modulating the non templated addition of nucleotides by reverse transcriptase enzymes such as MMLV-RT once it has reached the 5' end of the template (RNA). In case of RNAs, or any other nucleic acid, without a 5' protecting group, such as the cap, this results in blunt ends or ends with a 3' nucleotide overhang on the complementary (cDNA) strand. In contrast, in case of RNAs with a 5' protecting group such as the cap, the cap is provided as an overhang. When the protecting group is a triphosphate such as in bacterial mRNAs the nucleotide that carries this group will be provided as an overhang. This creates distinct structural differences that can be used to selectively ligate a linker to a cDNA that is in hybrid with an 5' protected RNA such as capped RNA or 5' triphosphate RNA. Specifically by using an adapter where the linker oligo has a 5' overhang and wherein this overhang can interact with overhang of the 5' protected RNA, by e.g. base pairing or base stacking in order to facilitate double strand specific ligation of the linker oligo to the 3' end of the cDNA. This is an example to achieve the selectivity in step d2) when labelling a complementary nucleic acid of a double strand dependent on the presence of the 5' protecting group on the template RNA strand. Double strand dependent ligation can be used to add the label or modification. Especially preferred, said labelling is specific for doubles strands where the RNA strand comprises the 5' protecting group, especially preferred wherein said 5' protecting group is an overhang at the RNA strand 5' end. The label can be a double stranded adapter nucleic acid provided with a 5' nucleotide overhang on a linker strand, and is ligated to said complementary nucleic acid. Such ligation can be performed using a double strand specific ligase. The adapter is an example of a nucleic acid label. In preferred embodiments, the 5' nucleotide overhang of the linker strand in the adapter consists of a single nucleotide. The overhang can be any nucleotide, such as A, G, C T but preferably is a C or a T, especially preferred a C.

In an (optional) step e) the presence of the label is tested. It is possible to enrich, select, isolate or purify nucleic acids with the label in comparison to nucleic acids without the label. The label can be used to amplify molecules where the label is present and/or to deplete molecules where the tag is absent, either on the complementary nucleic acid alone, separated from the template, or on the duplex, e.g. the cDNA::RNA hybrid. The label can e.g. be bound specifically by a label binding unit. Labels and label binding units can e.g. be an antigen/antibody pair, a ligand/receptor pair or hybridizing oligonucleotides with a complementary sequence. If the label is a sequence tag, then e.g. it is possible to enrich the labelled nucleic acid with specific amplification, e.g. by using a primer that binds to the label.

In a preferred embodiment the labelling step comprises ligating a nucleic acid sequence tag to said double stranded nucleic acid not modified in step c). Nucleic acid sequence tag can both be used for enrichment but also for later identification of particular complementary nucleic acids.

The modification of step c) preferably prevents labelling of said modified double strand in step d1). Examples are removing 3' terminal OH on the complementary strand from access for the labelling step in a protecting group- (on the template strand) dependent manner. Removing access may include digestion of at least 1 5' terminal nucleotides on the template strand, binding a blocking molecule to the 5' phosphate of the template strand, binding a blocking molecule to the 3' terminus (e.g. 3' OH) of the complementary strand or removal of the phosphate leaving a 5' OH terminus on the template strand.

Examples of such modifications are i) 5'-3' exonuclease digestion of nucleic acids without the protecting group, e.g. uncapped nucleic acids; ii) ligating the 5' end of the template strand to the 3' end of the complementary strand; iii) adding a nucleic acid lacking said label of step d1); or iv) removing 5' terminal phosphates on the template strand, preferably by phosphatase, especially preferred while the RNA still contains the 5' protecting group (in this embodiment preferably a 5' cap) and is thereby protected from 5' dephosphorylation.

Labelling is preferably a reaction that acts on blunt ends of the duplex of the protected RNA with the complementary nucleic acid. The blunt end is on the end with the protecting group. Thus, by creating overhangs either on the template or complementary strand on the modified non-protected nucleic acid duplexes, it is possible to mask these unwanted nucleic acids during labelling. Such overhangs are preferably at least 2 nucleotides in size, especially preferred 3, 4, 5, 6, 7, 8, 9, 10, or more, e.g. at least 15, at least 20, at least 30, at least 40 or at least 50 nucleotides.

E.g., if a double strand specific ligase is used in any step d) to ligate a sequence tag to the 3' end of the complementary strand (that has an active 3' OH), then the deactivation of the 3' end of the cDNA in step c) can be carried out by creating an overhang during reverse transcription of the templates and/or by digesting the 5' end sequence of the templates again creating a 3' overhang of the complementary nucleotide and/or by iii) ligating the 5' end sequence of the template to the 3' end of the complementary nucleic acid.

Blunt end specific ligases are not 100% depended on blunt ends. Especially in the case of nucleic acids with a protecting group, especially in case of a 5' cap, an overhang by 1 nucleotide on the template strand is also suitable for labelling. Thus, in a preferred embodiment said labelling is specific for double strands, preferably double strands with blunt ends or ends with at most 1 nucleotide overhang. For example the blunt end may comprise a capping nucleotide on the template strand followed by further nucleotides. The complementary strand may end with a nucleotide aligned with the further nucleotides up to—but not aligning with— the capping nucleotide. It is also possible that the complementary strand ends with a nucleotide that aligns with the cap. The aligning nucleotide may be complementary to the cap or not. Thus, the labelling step is specific for these end structures that are present in case of the RNA of interest but not in the duplexes with the other template nucleic acids after modification. In essence the modification removes structures that are selected for during labelling in the duplex nucleic acids with the templates without the 5' protecting group.

In preferred embodiments the complementary nucleic acid of an unmodified double stranded nucleic acid is labelled on the 3' end, preferably wherein the 3' terminal nucleotide of the complementary strand is annealed to the template strand with the 5' terminal nucleotide or the protecting group, preferably a 5' cap nucleotide, within 0 or 1 nucleotides of said 5' terminal nucleotide, especially in the case of a 5' polyphosphate, or the 5' protecting group, especially in the case of a 5' cap.

In preferred embodiments the inactivation of step c) is carried out at the end of the reverse transcription reaction by providing a non-capped template::complementary nucleic acid (usually RNA::cDNA) hybrid with a blunt end or a 3' overhang on the cDNA strand, thereby rendered inactive for subsequent labelling. In contrast a capped RNA::cDNA hybrid is provided with a cap overhang on the RNA strand, thereby rendered active for subsequent labelling. In that manner in step d2) a 5' overhang of a linker oligo in an adaptor will be ligated by a double strand specific ligase to the 3' end of a cDNA that is in a hybrid with a capped RNA but will not be ligated to a cDNA that is in a hybrid with a non-capped RNA.

It is preferred that the 5' overhang is a single nucleotide, and that this single nucleotide is a C. Furthermore it is preferred that the single nucleotide is phosphorylated on its 5' end or adenylated. This single nucleotide can align with the 5' protecting group, especially in case of a cap but also in case of polyphosphates (any single nucleotide N is suitable) and allow ligation of the adapter to the complementary strand.

Keeping this overhang in a protecting group selective manner can be controlled by low $Mn^{2+}$ or $Mg^{2+}$ concentrations or low dNTP concentration to prevent template independent C-addition of reverse transcriptase, which might negate the relevant initial differences between the protected RNA and the unprotected nucleic acid. Preferred conditions are e.g. combined $Mg^{2+}$ and $Mn^{2+}$ concentrations lower than 4 mM, preferably no $Mn^{2+}$, and/or lower than 0.4 mM of each dNTP, preferably lower than 0.25 mM, e.g. 0.1 mM.

According to option iv) described above it is also possible to remove 5' terminal phosphates on the template strand, especially monophosphates, e.g. with a phosphatase such as alkaline phosphatase. In option iv), a polyphosphate protecting group might also be removed. In order to prevent protecting group removal at this stage (it may of course later be removed when the non-protected duplex has been modified and thus "deactivated") it is preferred that a terminal phosphatase is used that is inactive on protecting group or only dephosphorylates monophosphates or to modify the polyphosphate protecting group for phosphatase resistance (e.g. replacement by another protecting group or strengthening the ester bonds against dephosphorylation). The RNA comprising the 5' protecting group is not modified by the phosphatase. This modification is also suitable to specifically label only the complementary nucleic acid aligned with the protected RNA. It is e.g. further possible to remove the protecting group leaving a monophosphate 5' end and adding a linker sequence that in turn can be used to hybridize a label to said linker that may consequently be ligated with the complementary nucleic acid aligned with the protected RNA. This step is in essence known from the Oligo Capping method mentioned in the background section. The vital difference to the present invention is that the modifications according to the invention are performed on the duplex, i.e. after creating the complementary nucleic acid, thereby conserving the sequence information of the RNA during modification within the duplex. Loss of information, especially on long RNA sequences as observed in the prior Oligo Capping method, are therefore avoided.

In preferred embodiments carried out according to i), the template::complementary strand hybrid is subjected to an exonuclease digestion step that degrades the RNA from 5' to 3'. Only RNA that comprises the 5' protecting group (e.g. cap structures or other blocking modifications, such as di- and triphosphates) are not degradable or resist degradation. Then, in any step d) a label is added to the 3' end of the complementary strand in dependence of the annealed 5' end of the RNA being present. This can for instance be achieved by a double strand specific ligase ligating an oligonucleotide to the 3' end of the cDNA.

The same effect can be achieved by option ii) by ligating the 5' end of the template strand to the 3' end of the complementary strand. This reaction can only be performed on nonprotected nucleic acids (e.g. without a 5' cap or 5' polyphosphate). Thus, the nucleic acids with the 5' protecting group remain unmodified. Subsequently only the 3' end of the complementary strands remain free for labelling, where said 3' ends have not been previously covalently linked to the aligned template strand.

According to option iii) it is also possible to simply add a further linker (or extension) to the 3' end of the complementary strand of the non-protected duplexes to block and inactivate said 3' ends. One option is to use a terminal transferase or more preferably extension activity of enzymes such as e.g. reverse transcriptase that acts only on non-protected blunt ends. After this step, the 3' ends of complementary strands that have previously been aligned to the RNA with the 5' terminus or the 5' protecting group (especially if it is a nucleotide as in a 5' cap) can be labelled according to any step d).

Thus, according to several of these options, the 3' OH on the complementary strand near the 5' terminus of the template is not accessible as in case of the duplexes without the protecting group. In case of a 5' protecting group being present in the duplex, the 3' OH remains accessible on the complementary strand. In the labeling step it is then possible to ligate the label to said 3' OH on the complementary strand which is near the protecting group on the template, e.g. aligned directly to the protected nucleotide or to the template within 1 nucleic acid distance of the protecting group as mentioned above.

According to the present invention the protecting group may or may not be removed. Preferably in options i), ii) or iii) for step c) the protecting group is not removed. In option iv) the protecting group is preferably removed—but preferably only after the modification of the non-protected nucleic acid duplexes in step c). According to the invention the modification is on duplexes without a protected nucleic acid. The 5' protecting group prevents the modification on the RNA of interest. Especially preferred the protecting group, e.g. in case of a 5' cap, is not oxidized throughout the steps of the invention.

According to the invention method step b) is carried out before step c), e.g. the reverse transcription of the RNA precedes the modification and selection process for certain RNA 5' ends. In that manner a degradation of the RNA by the selection process itself as described in the background section will not influence the quality and in particular the full length sequence aspect of the cDNA. Therefore a bias towards over or under representation of the longer or shorter RNA or a bias towards one end of the RNA molecules will be largely dependent on the qualities of the reverse transcription, but not the post-transcription events for selection. Many methods that reduce or influence the RT bias are known in the art such as the addition of trehalose and betain (11; 12), WO 2007/062445, US 2009/311754 A1, EP 11181546.0 (all incorporated by reference in their entirety)). Preferably the invention contains a full-length reverse transcription of RNA.

Any enzyme that has RNA dependent DNA or RNA polymerase activity can be used to create a reverse complement strand at the 5' end (TSS) of the template RNA, thus creating a double strand. In preferred embodiments the polymerase is an RNA dependent DNA polymerase. In other embodiments the polymerase is an RNA dependent RNA polymerase.

In an alternative embodiment this double stranded feature at the 5' end of the RNA can also be created by an oligonucleotide with a sequence complementary to the 5' end of the RNA, e.g. by annealing of complementary nucleic acid molecules, in total or in part and then ligating to a complementary nucleic acid portion at the 5' end.

Terminal Transferase Activity of RT:

It is known that reverse transcriptases add extra nucleotides when they reach the 5' end of the RNA template in a terminal transferase-like manner. If reverse transcriptions are carried out in a manner that these extra nucleotides are added only when the protecting group is not present, they will aid the selection process by the double strand specific ligase later on. For instance, a lower $Mg^{2+}$ concentration can be used to add less non-template nucleotides. Especially preferred are $Mg^{2+}$ at or below 3 mM, preferably below 2.5 mM. Another way to cause less non-template nucleotide addition is to lower dNTP concentrations. It is therefore preferred that the reverse transcriptase has inhibited, e.g. reduced or no, terminal transferase activity or conditions are used that reduce or inhibit this activity. Especially preferred, in step b1) a reverse transcriptase enzyme is used that has inhibited terminal transferase activity or conditions are used that cause a reduction of this activity as compared to a non-modified reverse transcription at more than 3 mM $Mg^{2+}$ with abundant dNTPs.

Digestion of 3' cDNA Overhangs:

If during RT complementary nucleic acid strand overhangs are also created at the 5' end of RNAs that should be selected for in step c) through e.g. double strand specific ligation, these 3' overhangs of the cDNA can be digested using an enzyme with a preferable single strand specific 3'-5' exonuclease activity such as Exonuclease T, Exonuclease T5, Shrimp Nuclease, Mung Bean Nuclease or DNA Polymerase I Large (Klenow)Fragment) to make the cDNA available for double strand specific ligation of any step d). It is therefore preferred that a 3' cDNA overhang is digested prior to any step d).

RNAse H Activity of RT:

When a reverse transcriptase is used to create the complementary nucleic acid strand to the RNA it is preferred that the RT has a reduced or no RNAse H activity. An RNAse H activity will create nicks in the RNA and the RNA might under unfavorable conditions dissociate from the cDNA and thus render the 3' end of the cDNA inactive for a double strand specific ligation. It is therefore highly preferred that the reverse transcriptase has no or reduced RNAse H activity or that conditions are used that reduce or inhibit this activity. RNAse H activity can be reduced by removal of the RNAse H domain of the transcriptase or by mutations reducing or inhibiting its activity. Thus, preferably in step b1), a reverse transcriptase enzyme is used that is modified, wherein said modification reduces or inhibits the RNAse H activity of the reverse transcriptase enzyme.

Spurious Second Strand Synthesis:

As reverse transcriptases are able to prime second strand synthesis using free 3' cDNA ends that would render these cDNAs inactive, it is preferred that second strand synthesis is inhibited. For instance Actinomycin D can be used to inhibit second strand synthesis.

Protection of the RT Primer:

When an exonuclease is used that would also digest the cDNA in a 5'-3' direction, the RT primer needs to be resistant to the exonuclease. There are many ways known in the art to exert exonuclease resistance onto an oligonuclotide. For instance, one or more phosphorothioate (PTO) or locked nucleic acid (LNA) modifications can protect the primer from exonuclease digestion. Preferably these modifications should be near or at the 5' end of the primer. Other modifications that could be used are for instance 5' blockers such as C3, C9, C12 spacers or 5' labels such as biotin that reduce, inhibit or block the 5'-3' exonuclease activity. For double strand specific exonucleases also a 5' overhang to the priming sequence of the oligonucleotide can be introduced, so that the 3' part of the priming oligonucleotide is in a hybrid with the RNA and the 5' part stays single stranded. In a preferred embodiment the oligonucleotide primer is resistant to 5'-3' exonuclease digestion.

Post RT Ligation:

As described the inactivation of the 5'-phosphate of a (non-protected) nucleic acid molecule can be carried out by ligating this 5'phosphate to the 3' OH of the complementary strand effectively inactivating the 3' OH of the complementary strand for double strand specific labeling as carried out in any step d). If it is used in conjunction with a 5'-3' exonuclease step, this ligation can be carried out either before or after the exonuclease step, but before the double strand specific ligation of any step d).

Post RT Phosphorylation:

For 5'-3' exonuclease digestion different enzymes can be used, having different activities on different nucleic acids, e.g. RNAs, and their ability to digest 5' phosphate, 5' OH and 5' triphosphate. If it is desired to deactivate also the 3' end of a complementary nucleic acid strand, in particular a cDNA, in a hybrid with a nucleic acid molecule with a 5' OH, a 5'-3' exonuclease is preferably used that cannot start to digest from a 5' OH, but is specific for a 5' phosphate. Then, the 5' OH of the nucleic acid, e.g. RNA, can be turned into a 5' phosphate by phosphorylation. Phosphorylation can be carried out by e.g. a Polynucleotide Kinase, such as Optikinase (Affymetrix). It is therefore preferred that a 5' OH of a nucleic acid, e.g. an RNA, is converted to a 5' phosphate, when an exonuclease is used that is active on 5' phosphorylated nucleic acid, preferably after step b). The nucleic acid is preferably non-protected.

Pre Exo Dephosphorylation:

If a 5'-3' exonuclease is used, which is only active on 5' OH nucleic acids, a dephosphorylation step previous to the exonuclease digestion reaction can be carried out. Any kind of phosphatase such as shrimp alkaline phosphatase, antarctic phosphatase or calf intestinal alkaline phosphatase can be used. It is therefore preferred that a 5' phosphate of a nucleic acid, preferably an RNA, is converted to a 5' OH, when an exonuclease is used that is active on 5' OH. The nucleic acid is preferably non-protected.

EXO Digestion:

In principle, any enzyme that has a 5'-3' exonuclease activity on the nucleic acid, preferably hybridized to a complementary strand, can be used. The nucleic acid may be RNA, especially non-protected RNA, and the complementary nucleic acid may be its cDNA. Exonucleases that have a 5'-3' activity are for instance T7 exonuclease, T5 exonuclease, Lambda exonuclease, terminator exonuclease, XRN-I exonuclease and others. Polymerases with 5'-3' exonuclease activity are for example Bst polymerase, Taq polymerase, *E. coli* DNA polymerase I.

Additives that can enhance the activity of such exonuclease such as thermal stabilizers and activators as well as crowding agents can be used. Crowding agents are inert molecules that can be used in high concentrations and can be used to mimic the effects of macromolecular crowding inside a cell. Examples are PEG (polyethylene glycol), PVP (polyvinylpyrrolidone), trehalose, ficoll and dextran. Crowding agents are e.g. disclosed in U.S. Pat. No. 5,554,730 or 8,017,339.

Thermal stabilizers such as trehalose are known to enhance the activity of nucleases such as DNAse I (11).

As the conformation of a DNA::RNA hybrid might not be optimal for exonucleases preferring DNA::DNA hybrids, the addition of a crowding agent such as PEG might boost the reaction by changing conformation and/or by volume exclusion. In preferred embodiments of the invention the exonuclease digestion is carried out with the addition of agents that change nucleic acid conformation and/or activate the exonuclease, such as a crowding agent, like trehalose or PEG.

Ligation:

The ligation for labeling in any step d) can be carried out with any double stranded specific ligase that will ligate the 3' OH of the complementary nucleic acid, e.g. a cDNA, that is in a double strand such as a cDNA::RNA hybrid to the 5' phosphate of a sequence tag such as a single stranded linker or double stranded adaptor. For instance T4 DNA ligase, T4 RNA ligase 2, and T4 RNA ligase 2 truncated, that is preferably devoid of the adenlylating domain, are good ligases for the purpose of the invention.

Additives that can enhance the activity, such as thermal stabilizers and activators, such as trehalose, can be used. In addition crowding agents, such as PEG or any one of the above, that also can improve double strand conformation can be used as well as different divalent cations, such as magnesium chloride or manganese chloride.

In preferred embodiments any step d) comprises the double strand specific addition of a sequence tag or linker sequence to the 3' OH of the cDNA, which is preferably carried out with a double strand specific ligase, such as T4 DNA ligase, T4 RNA ligase 2 or T4 RNA ligase 2 truncated. As pyrophosphate can inhibit enzymes such as polymerases and (other) ligases, the addition of pyrophosphatase is preferred.

Label to be Added to the cDNA:

The label can be any molecule or group that can label a cDNA. It is preferred that the label is an oligonucleotide linker.

Oligonucleotide Linker for Tagging:

The oligonucleotide can be of any nucleic acid such as DNA, RNA, LNA, PNA or any substitute currently used in the art in any combination. The 5' end of the oligonucleotide needs to be accessible for ligation. Different ligases require different 5' ends such as 5' OH or 5' phosphate. Most ligases use a 5' phosphate that is activated through adenylation or guanylation. Most ligases adenylate a 5' phosphate. In preferred embodiments the oligonucleotide that is ligated is preadenylated at its 5' end.

Reverse Complement to Linker:

As double strand specific ligases prefer also a double strand on the donor side (5' phosphate), it is preferred that at least the 5' end of the linker is in a double strand with an oligonucleotide of reverse complement sequence. Generally speaking such double stranded linkers are called adapters. As described above, the reverse complement can be of any nucleic acid or analogue known in the art. It is preferred that the linker is provided as an adapter. In preferred embodiments the nucleic acid sequence tag is at least partially double stranded, in particular preferred at the ligation end (the 5' end where the ligation results in a covalent connection to the complementary nucleic acid).

As any free 3' OH can potentially serve as an acceptor during polymerization or ligation, it is preferred that a free 3' OH of the linker or adapter oligonucleotides is blocked. Many blocking groups are known in the art. Provided for reference but not limiting are dideoxynucleotides, C-spacers and phosphate groups. It is preferred that any free 3' OH of the adapter oligonucleotides is blocked.

Fluorescent Label:

The complementary nucleic acids can be labeled with any molecule known in the art. For instance fluorescent molecules such as e.g. fluorescin or biotin can be used to act as either direct or indirect reporters. It is preferred that the oligonucleotide tag or the reverse complement are labeled.

Selection for the Labeled Nucleic Acids by Solid Phase Purification:

One method to enrich labeled molecules, e.g. with the nucleic acid sequence tag is to use the nucleic acid sequence tag to carry out a solid phase selection such as e.g. a bead selection. For instance, beads with an avidin surface can be applied and a label with biotin can be used to bind to the avidin surface. However, any other label binding system can be used, such as antigen antibody binding. Also an oligonucleotide with a reverse complement sequence capable of hybridizing the nucleic acid sequence tag can be attached to a bead.

It is preferred that the labeled complementary nucleic acid is purified through solid phase binding or selection, preferably on a bead. Also preferred, the nucleic acid sequence tag or the reverse competent oligonucleotide or the adapter is bound to the bead and the double strand specific ligation is carried out with the label attached to the bead. It is preferred that the label is immobilized, e.g. attached to a solid surface, e.g. directly or via hybridization to an attached reverse complement oligonucleotide, and the labeling reaction of any step d) is carried out on the solid phase.

Selection for Labeled Nucleic Acids by Exonuclease Digestion:

Another possibility to purify the labeled complementary nucleic acid is to digest all nucleic acids that have no tag. For instance, a 3'-5' exonuclease digestion can be carried out. In this case that label needs to be 3'-5' exonuclease resistant. Oligonucleotides can be made exonuclease resistant through many means. For instance, the addition of a 3' blocking group such as C3, C6, C9 or C12 or biotin can exert such protection. Furthermore, PTOs or LNAs can reduce or inhibit exonucleolytic degradation.

It is preferred that the labeled complementary nucleic acid is purified by depleting nucleic acids that have no label, preferably by 3'-5' exonucleolytic digestion, wherein the label provides protection from digestion.

It is known that during RT a template switch can occur to any other nucleic acid. As the RT primer is provided in excess over the template RNA, the RT primer may template switch adding a poly A sequence to the 3' end of the complementary nucleic acid. When an amplification reaction, such as a PCR, is used to amplify the complementary nucleic acid, the second primer that can hybridize to the reverse complement of the RT primer will alone amplify such RT primer primed and template switched complementary nucleic acids, thus creating a background that is unspecific to the to be selected 5' end of the RNA. To reduce this background the RT primer may have no protective end modification such as C3 or biotin on its 5' end. Also, the RT primer may have no internal modification such as PTOs or LNAs. However, the RT primer can have a 5' overhang that will not hybridize to the RNA. In that manner the 5' overhang will protect the complementary nucleic acids in a 5'-3' double strand specific exonuclease digestion (step c) (i)). However, when the RT primer is used as a template for template switch, the template switched RT primer is not protected from this exonuclease digestion. This is because the RT primer is in a hybrid with the 3' end of the complementary nucleic acid and therefore available for 5'-3' exonuclease digestion. In that manner a 3' cDNA overhang is created during step c) for all template switched complementary nucleic acid inhibiting the double strand specific labeling of any step d) and therefore reducing this background when a subsequent selection for the label is carried out.

For instance, the reverse complement oligonucleotide to the nucleic acid sequence tag in the adapter can have a modification to its 5' end that enables a positive selection for this modification, such as a biotin tag for an avidin bead based selection or the linker tag itself has a modification that protects it from a 3'-5' based exonuclease digestion as described above.

It is preferred that the oligonucleotide primer has a 5' overhang and that one or both strands of the nucleic acid sequence tag has a modification for positive selection or the nucleic acid sequence tag is protected from nuclease digestion.

Selection for the Labeled Nucleic Acids by Specific Polymerization:

When a nucleic acid sequence tag is added as a label, specific copying (amplification) can be carried out. For instance, a specific amplification using a primer extension reaction with a primer that can hybridize to the nucleic acid sequence tag can be carried out. Thus, the complementary nucleic acid that is labeled is copied. Such a reaction can be carried out through many cycles with a linear amplification or using a second primer specific for a complementary nucleic acid resulting in an exponential amplification, such as in a PCR. If all polyadenylated RNA is to be amplified, it is preferred that the second primer has a poly T stretch.

In other embodiments of the invention, the complementary nucleic acid, e.g. being at least partially double stranded as in an adapter, can provide for a promoter that can initiate nucleic acid dependent nucleotide polymerization. For instance, the adapter can provide for a T7, T3 or SP6 promoter and a specific DNA dependent RNA polymerase can be used to copy the complementary nucleic acid. It is therefore preferred that the labeled nucleic acid is amplified through specific template dependent nucleotide polymerization.

ABBREVIATIONS

TSS: transcription start site, PTO: phosphorothioate bond, LNA: locked nucleic acid, RT: reverse transcription or reverse transcriptase (depending on the context), PNA: peptide nucleic acid, PCR: polymerase chain reaction.

The present invention is further illustrated by the following figures and examples without being limited to these specific embodiments of the invention.

FIGURES

FIG. 1A:
Schematic representation of one embodiment of the invention, where a cDNA molecule is labeled on its 3' end with a nucleic acid sequence tag only when a cap is present on the template RNA molecule.

a) mRNA(i) that has a 5' cap and rRNA (ii) that has a 5' phosphate are primed with a random primer P and reverse transcribed to b) generate RNA::cDNA hybrids. c) These hybrids are exposed to a 5'-3' specific exonuclease digesting the RNA strand from the 5' end when a 5' phosphate is present but not when a cap is present, thereby digesting the 5' ends of rRNA but not mRNA. In step d1) a nucleic acid sequence tag L is ligated to the 3' end of the cDNA using a double strand (ds) specific ligase. Only cDNAs with their 3' end-sequence still in a hybrid with the 5' end-sequence of their RNA are participating in the ligation. Therefore, e) only the cDNAs of mRNA molecules whose cap protected them from exonuclease digestion have been tagged with oligonucleotide L.

Figure 1B:
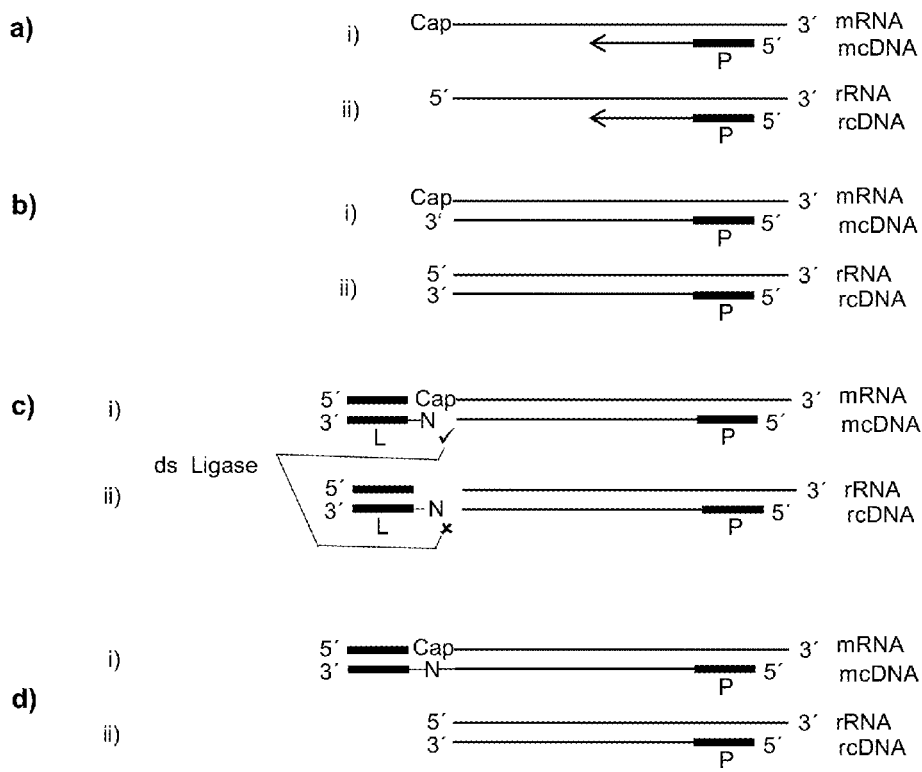

FIG. 1B:
Schematic representation of an alternative embodiment of the invention, whereby—pending the presence of a cap on the template RNA—a cDNA molecule is labeled on its 3' end using a double-stranded adapter with a 5' overhang.

a) Similar to FIG. 1A, mRNA (i) that has a 5' cap and rRNA (ii) that has a 5' phosphate are primed with a random primer P and reverse transcribed to b) generate RNA::cDNA hybrids. c) a nucleic acid sequence tag L in form of a double-stranded adapter with a single nucleotide 5' overhang at the ligation site is ligated to the 3' end of the cDNA using a double strand (ds) specific ligase. Only cDNAs with their 3' end-sequence still in a hybrid with the 5' end-sequence of their RNA but not extending to the cap structure or beyond are participating in the ligation. Therefore, d) only the cDNAs of mRNA molecules whose cap provided for the adapter ligation have been tagged with oligonucleotide L.

Figure 2A:
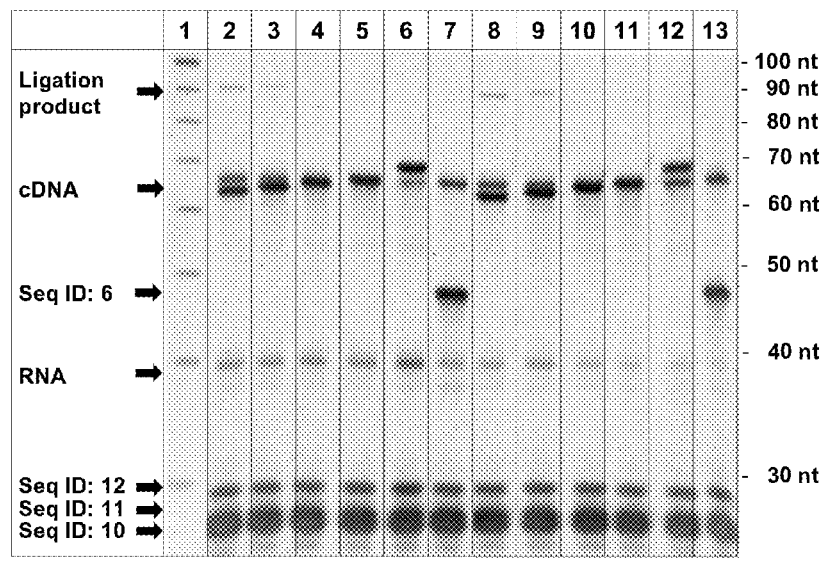

FIG. 2A:
Depicts the results of Example 1A. Double strand specific ligation with T4 RNA ligase 2 (truncated) on c0/c1 capped artificial RNA hybridized to cDNAs of different lengths.

Figure 2B:
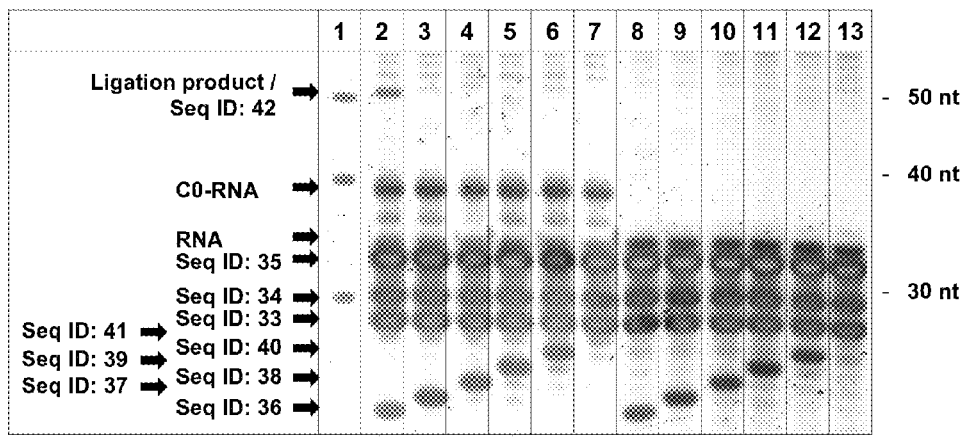

FIG. 2B:
Depicts the results of Example 1B. Double strand specific ligation with T4 DNA ligase on c0 capped or non-capped artificial RNA hybridized to cDNAs of different lengths.

Figure 3:
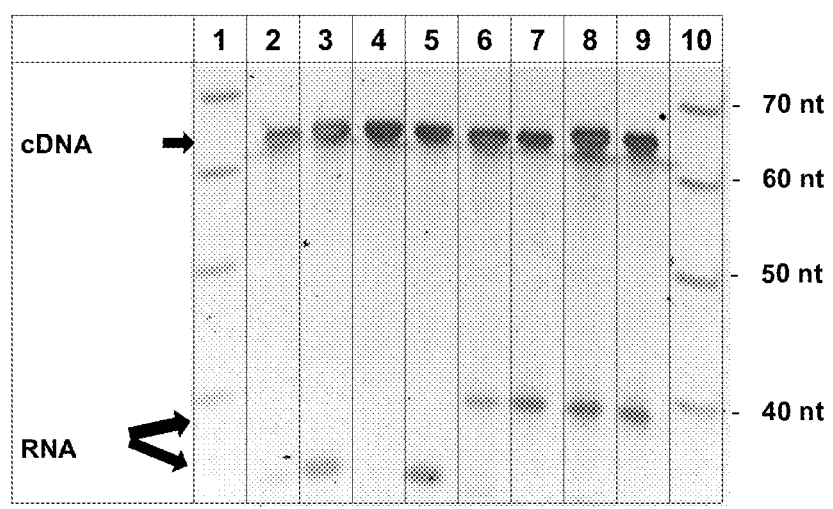

FIG. 3:
Depicts the results of Example 2: T7 Exonuclease digestion of artificial RNA/cDNA hybrids.

FIG. 4:
Reverse transcription and Cap dependent ligation of a nucleic acid sequence tag to an mRNA::cDNA hybrid.

a) Illustrates the assay setup. An RNA molecule (Seq ID: 3-5, 7, 8) is primed with a 5' PTO protected primer (Seq ID: 6) that is extended during an RT reaction to yield a cDNA (Seq ID: 9). A linker oligonucleotide (Seq ID: 11) that is in a hybrid with its reverse complement sequence (Seq ID: 12) is ligated to the cDNA to yield a linker tagged cDNA molecule (Seq ID: 13).

b) and c) show the results of Example 3.

Figure 5A:
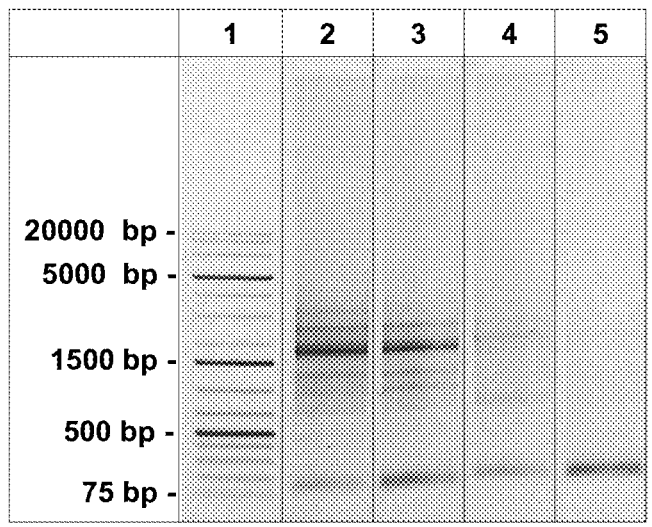

FIG. 5A:
Depicts the results of Example 4: PCR amplification products on treated or untreated (XRN-1, TAP) cDNA samples.

Figure 5B:
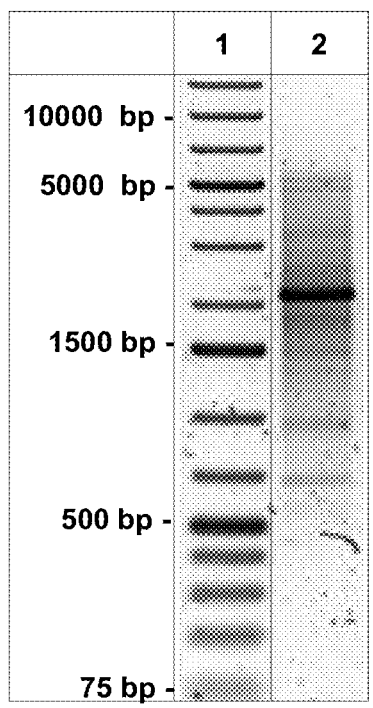

FIG. 5B:
Depicts the result of Example 4B: PCR amplification products of a cDNA sample tagged in an alternative embodiment.

EXAMPLES

Example 1A: Investigating Double Strand Specific Ligation Using Artificial RNA Molecules of Defined Sequence As the cap presents a structure that is in its essence a guanosine that is methylated on the N7 of the purine ring and linked on its 5' end to the 5' end of the RNA through a triphosphate bridge, it was previously not known if a label could be ligated in a double strand specific manner to a cDNA in a hybrid with such a capped RNA. Therefore, in an artificial assay capped T7 transcripts together with oligonucleotides with different 3' overhangs or 3' missing nucleotides were set up in a ligation reaction to investigate if such double strand specificity could be reached. Of special interest was if an extra nucleotide on the cDNA would be needed that could base pair or stack with the cap.

Ligation:

Different oligonucleotides representing the cDNA with different 3' extensions (Seq ID: 22-26) were ordered from Microsynth AG (Balgach, CH), are reverse complements to the RNAs (Seq ID: 4, 5) with a 28 nt PTO protected 5' overhang. While Seq ID: 22 has no 3' extension, Seq ID: 23 has an extra 3' C added to be hybridized to the cap structure. The other cDNAs resemble the nontemplated nucleotide addition (preferably Cs) and have further 1 (Seq ID: 24), 2 (Seq ID: 25) or 5 (Seq ID: 26) Cs added. To imitate a break off product of the RT transcribing the RNA, also the RT-primer (Seq ID: 6) was used as a cDNA template.

For the generation of the 33 nt in vitro transcribed RNA templates (Seq ID: 4, 5) see Example 3. Ligation was carried out in a 20 µl reaction using 2 pmol c0 (Seq ID: 4) or c1 (Seq ID: 5) RNA, mixed with 9.76 pmol of double stranded preadenylated adaptor (Seq ID: 11, 12) and 2 pmol of the different cDNAs (Seq ID: 6, 22-26). For the preadenylation reaction of the linker oligo (Seq ID: 10) see Example 3. All required components including buffer (50 mM Tris (pH 7.8), 10 mM MnCl2, 5 mM DTT), 20 U RNasin Ribonuclease Inhibitor (Promega Corporation, Wisconsin, USA), 0.033 U PPase (Fermentas GmbH, St. Leon-Rot, Germany), 20% PEG 8000 and 200 U T4 RNA ligase 2, truncated (New England Biolabs GmbH, Frankfurt am Main, Germany) were added and incubated at 25° C. for 3 h. After silica purification using silica well plate (Binding buffer=20% (v/v) Gu-HCl/80% (v/v) EtOH, Wash Buffer=20% (v/v) 100 mM Tris, 400 mM NaCl pH 7.5/80% (v/v) EtOH, elution buffer=10 mM Tris pH 8.0) the whole reactions were mixed with 100% formamide loading buffer, denatured at 95° C. for 2 min, cooled on ice and resolved by electrophoresis in a 15% acrylamide/7M urea gel.

Results are shown in FIG. 2A: In the different lanes the different cDNAs are depicted, showing in lane 2, 8 Seq ID: 22, lane 3, 9 Seq ID: 23, lane 4, 10 Seq ID: 24, lane 5, 11 Seq ID: 25, lane 6, 12 Seq ID: 26 and in lane 7, 13 Seq ID: 6 with either c0 capped RNA (Seq ID: 4) in lane 2-7 or c1 capped RNA (Seq ID: 5) in lane 8-13. In lane 1 100 ng of 10 by DNA ladder (Life Technologies Corporation, New York, USA) are loaded. Depending on the cDNA, ligation will result in a 88-94 nt desired ligation product, but as seen in FIG. 2A the product just appears when the cDNA just has one or no extra C on its 3' end, showing a 88 nt product (Seq ID: 27) in lane 2, 8 and a 89 nt product (Seq ID: 28) in lane 3, 9, therefore no ligation should take place to the cDNA even if in the exonuclease digestion step the RNAs were not completely digested. Furthermore, no ligation of the linker to the RT-primer could be observed, indicating that the linker also does not ligate to cDNA break off products generated during RT. As a ligation product is only visible in certain reactions and no ligation can be seen when a cDNA overhang exists, the ligation is double strand specific. Same results are obtained with c0 and c1 capped RNA. It is also important to note that a linker can be ligated to the cDNA whether or not an extra nucleotide (C) is added to the cDNA in dependence of the cap. Therefore the RT needs to be adjusted to preferably add no or only one nucleotide when reaching the cap of RNAs.

Example 1B: Investigating Double Strand Specific Ligation of an Adapter with a 5' Overhang to a Capped or Non-Capped RNA::cDNA Hybrid If, as raised above, during reverse transcription of capped RNA (mRNA) a reverse transcriptase preferably adds no additional nucleotide (C) to the cDNA then the cap will provide for a one nucleotide overhang. However, this cap overhang will consist of an inverted nucleotide that is furthermore connected through a triphosphate bridge to 5' end of the RNA. Therefore it was investigated if this cap overhang can interact (e.g.: base stack or base pair) with a 5' overhang of an adapter in a manner that enables double strand specific ligation of a linker oligo to the 3' end of the cDNA.

In contrast to the capped RNA, if the reverse transcriptase reaches the 5' end of non-capped RNA it will leave ether a blunt end or add additional nucleotides to the cDNA in a non template fashion. Therefore, control reactions where included where the non-capped RNA was in hybrid with a cDNA that leaves a blunt end or a cDNA overhang. Here a double strand specific ligase should not ligate an adapter with a 5' overhang to the cDNA.

In summary, if an adapter with a 5' overhang could be ligated to such a capped RNA:cDNA hybrid but not to a non-capped RNA:cDNA hybrid then this would provide for a selection mechanism for cDNA that was generated from capped RNA.

Ligation:

Different oligonucleotides representing the cDNA with different 3' extensions (Seq ID: 36-41) were ordered from Microsynth AG (Balgach, CH). They are reverse complements to the RNA (Seq ID: 4) and 26-30 nt in length. While Seq ID: 36 has no 3' residue matching the cap-structure, Seq ID: 37 has an extra 3' C added that can base pair or stack with the cap structure. The other cDNAs resemble the non-templated nucleotide addition (preferably Cs) and have further 1 (Seq ID: 38), 2 (Seq ID: 39), 3 (Seq ID: 40) or 4 (Seq ID: 41) Cs added.

For the generation of the 33 nt in vitro transcribed RNA templates (Seq ID: 4) see Example 3. Ligation was carried out in a 20 µl reaction using 2 pmol c0 (Seq ID: 4) or non-capped (Seq ID: 3) RNA, mixed with 20 pmol of double stranded preadenylated adaptor (Seq ID: 34, 35) and 2 pmol of the different cDNAs (Seq ID: 36-41). For the preadenylation reaction of the linker oligo (Seq ID: 34) see Example 3. All required components including buffer (50 mM Tris (pH 7.5), 10 mM MgCl2, 1 mM ATP, 10 mM DTT), 20 U RNasin Ribonuclease Inhibitor (Promega Corporation, Wisconsin, USA), 0.033 U PPase (Fermentas GmbH, St. Leon-Rot, Germany), 20% PEG 8000 and 400 U T4 DNA ligase (New England Biolabs GmbH, Frankfurt am Main, Germany) were added and incubated at 25° C. for 3 h. After silica purification using silica well plate (Binding buffer=20% (v/v) Gu-HCl/80% (v/v) EtOH, Wash Buffer=20% (v/v) 100 mM Tris, 400 mM NaCl pH 7.5/80% (v/v) EtOH, elution buffer=10 mM Tris pH 8.0) the whole reactions were mixed with 100% formamide loading buffer, denatured at 95° C. for 2 min, cooled on ice and resolved by electrophoresis in a 15% acrylamide/7M urea gel.

Results are shown in FIG. 2B: In the different lanes the different cDNAs are depicted, showing in lanes 2-7 and lanes 8-13 sets of Seq IDs: 36-41 each. The reaction contained either c0 capped RNA (Seq ID: 4, lanes 2-7) or non-capped RNA (Seq ID: 3, lanes 8-13). In lane 1 100 ng of 10 by DNA ladder (Life Technologies Corporation, New York, USA) is loaded. Depending on the cDNA, ligation will result in a 50-55 nt desired ligation product. As seen in FIG. 2B the product exclusively appears as 50 nt band (Seq ID: 42) in the reaction with c0 RNA and a cDNA (Seq ID: 36) lacking any nucleotide opposite of the RNA's cap structure position. The reactions with non-capped RNA (Seq ID: 3) did not yield any ligation product (lanes 8-13). This indicates that ligation does not take place at non-capped RNA but at capped RNA, and with a cDNA not extending beyond a position complementary to the +1 residue of the RNA immediately downstream of the cap structure. Any non-template nucleotide addition in the RT resulting in a cDNA such as Seq ID 36-41 will not be ligated. The lack of aberrant ligation products in lanes 3-13 also indicates that the ligation is double-strand specific.

Example 2: T7 Exonuclease Digestion of Artificial RNAs Having Different 5' Ends To show the specificity of the exonuclease digestion for different 5' ends of RNAs when in hybrid to different cDNA molecules, an experiment was carried out using artificial oligonucleotides.

Hybridization:

The template for the T7 Exonuclease digestion was done on PAGE-purified hybrids of the RNA (Seq ID: 4, 7, 8) to different oligos resembling the cDNA (Seq ID: 22, 23). The different RNAs (Seq ID: 7, 8) were ordered from Eurogentec (Seraing, Belgium). Hybridization was done by heating the RNA and oligos in 10 mM Tris pH 7.0 up to 95° C. for 30 sec with cooling down to 45° C. with a ramp speed of 2% (an ABI9700 thermal cycler) and addition of equal volume 2× Hybridization buffer (100 mM Tris pH 7.9, 6 mM MgCl). After a hold of 15 min the temperature was further decreased with a ramp speed of 2% down to 4° C. Following hybrids were synthesized: Seq ID: 4/Seq ID: 22, Seq ID: 4/Seq ID: 23, Seq ID 7/Seq ID: 22, Seq ID: 8/Seq ID: 22 and PAGE purified on a native 15% acrylamide gel.

T7 Exonuclease Digestion:

In a 20 µl reaction 50 ng of all hybrids were mixed with all required components including buffer (20 mM Tris-acetate, 50 mM potassium acetate, 10 mM Magnesium Acetate, 1 mM DTT, pH 7.9 @ 25° C.) and 20 U of T7 Exonuclease from New England Biolabs GmbH (Frankfurt am Main, Germany) (10 U/µl). The reaction was carried out at 37° C. for 30 min and silica purified using silica well plate (Binding buffer=20% (v/v) Gu-HCl/80% (v/v) EtOH, Wash Buffer=20% (v/v) 100 mM Tris, 400 mM NaCl pH 7.5/80% (v/v) EtOH, elution buffer=10 mM Tris pH 8.0)). The whole reactions were mixed with 100% formamide loading buffer, denatured at 95° C. for 2 min, cooled on ice and resolved by electrophoresis in a 15% acrylamide/7M urea gel.

Results are shown in FIG. 3:

In the different lanes the different hybrids consisting of different RNAs (Seq ID: 4, 7, 8) hybridized to different cDNAs (Seq ID: 22, 23) are shown. Lane 2, 4, 6, 8 show the hybrids after the exonuclease digestion while for lane 3, 5, 7, 9 no reaction was carried out. RNA with 5' OH (Seq ID: 8) with Seq ID: 22 was put in lane 2, 3, RNA with 5' P (Seq ID: 7) with Seq ID: 22 in lane 4, 5, and RNA with 5' cap (Seq ID: 4) with Seq ID: 22 in lane 6, 7, and with Seq ID: 23, to imitate an extra nucleotide addition for the cap through the reverse transcription, in lane 8, 9. 100 ng of GeneRuler™ 1 kb Plus DNA Ladder from Fermentas GmbH (St. Leon-Rot, Germany) are shown in lane 1 and 10.

After digestion all cDNAs remain in the reaction, while RNA with 5' P (lane 4) gets completely digested, while >95% gets digested of the 5' OH RNA (lane 2). For the capped RNA a difference is seen depending on the length of the cDNA. Is the cDNA blunt ended with the RNA (Seq ID: 22) the capped RNA gets partially digested (lane 6), while there is a better protection against exonuclease digestion when the cDNA contains an extra nucleotide for the cap structure to hybridize or stack with (Seq ID: 23), lane 8.

Example 3: Proof of Concept Using Artificial RNA Molecules

To investigate the specificity and sensitivity of preferred embodiments of the invention a proof of concept experiment is shown in an assay using RNA molecules of defined sequence. For an outline of the assay setup see FIG. 4a and for results see FIGS. 4b and c.

Generation of in vitro transcribed 33nt RNA templates:

The template for the T7 in vitro transcription was generated by hybridization of two oligonucleotides (Seq ID: 1, 2) one containing a T7 promoter sequence. Hybridization was done by heating the oligonucleotides in 10 mM Tris pH 8.0 up to 95° C. for 30 sec with cooling down to 45° C. with a ramp speed of 2% (on an ABI9700 thermal cylcer) and addition of an equal volume 2× Hybridization buffer (100 mM Tris pH 7.9, 6 mM MgCl). After a hold of 15 min the temperature was further decreased with a ramp speed of 2% down to 4° C. This template was then used for T7 in vitro transcription using Epicentre's AmpliScribe T7 High Yield Transcription Kit (Epicentre® Biotechnologies, Wisconsin, USA) and was PAGE purified afterwards. The 33 nt in vitro transcribed RNA (Seq ID: 3) with a 5' triphosphate was further c0 (Seq ID: 4) and c1 (Seq ID: 5) capped using ScriptCap m7G Capping System including ScriptCap 2'-O-Methyltransferase.

cDNA Synthesis:

First-strand cDNA synthesis was carried out using MMLV-H Point Mutant from Promega Corporation (Wisconsin, USA)(200 U/µl). A 5'-PTO protected sequence specific primer for cDNA synthesis (Seq ID: 6), was ordered from Microsynth AG (Balgach Switzerland). In individual 20 µl reactions 2 pmol the different RNAs (Seq ID: 3-5, 7, 8) and 4 pmol oligo (Seq ID: 6) were mixed with all required components including 50 mM Tris-HCl (pH 8.3), 75 mM KCl, 3 mM MgCl$_2$, 10 mM DTT), 0.5 mM of each dNTP, 20 U RNasin Ribonuclease Inhibitor (Promega Corporation, Wisconsin, USA) and 200 U of reverse transcriptase. For RNA with 5' OH (Seq ID: 8) 0.5 mM rATP and 1 U Optikinase from Affymetrix (California, USA, 1 U/µl) was added to the reaction mixture. The reaction was started at 37° C. for 4 min followed by 46° C. for a 30 min hold, resulting in a 55 nt long cDNA (Seq ID: 9). Following first strand synthesis samples were silica purified using a 96-well silica plate (Binding buffer=20% (v/v) Gu-HCl/80% (v/v) EtOH), washed twice with Wash Buffer=20% (v/v) 100 mM Tris, 400 mM NaCl pH 7.5/80% (v/v) EtOH) and eluted in 12 µl of 10 mM Tris pH 7.0.

5'-3' Exonuclease Digestion:

The cDNA (Seq ID: 9): RNA (Seq ID: 3-5, 7, 8) hybrids were exposed to 5'-3' exonuclease digestion using either XRN-1 (1 U/µl) or Lambda Exonuclease (5 U/µl) from New England Biolabs GmbH (Frankfurt am Main, Germany). The XRN-1 reaction was carried out in 20 µl and contained 50 mM Tris-HCl (pH 7.9 @ 25° C.), 100 mM NaCl, 10 mM MgCl$_2$, 1 mM DTT, 20% PEG 8000 and 1 U of enzyme, while for Lambda Exonuclease the reaction components included 67 mM Glycine-KOH (pH 9.4 @ 25° C.), 2.5 mM MgCl$_2$, 50 µg/ml BSA, 20% PEG 8000 and 15 U of Lambda Exonuclease in 30 µl. Both reaction were carried out at 37°

C. for 60 min and silica purified using a 96-well silica plate (Binding buffer=20% (v/v) Gu-HCl/80% (v/v) EtOH, Wash Buffer=20% (v/v) 100 mM Tris, 400 mM NaCl pH 7.5/80% (v/v) EtOH, elution buffer 10 mM Tris pH 7.0).

Preadenylation of Oligonucleotides:

This step was carried out according to Lau, et al (13). In short: Imp A was prepared by addition of 15 ml of 33.3 mM Adenosine-5'-monophosphate, free acid (in N,N-Dimethylformamide) to 15 ml of reagent mix (consisting of 66.67 mM Triphenylphosphine, 66.67 mM 2,2'-dipyridisulfide (=Aldrithiol-2), 166.7 mM Imidazole and 433 mM Triethylamine in N,N-Dimethylformamide) and stirred for 2 h at room temperature. Afterwards the reaction solution was added to the vigorously stirred precipitation buffer (340 ml consisting of 26.5 mM NaClO$_4$, 66.18% Acetone and 33.82% Diethylether) and ImpA will precipitate. The precipitate weight was equalized with acetone and centrifuged at 3,000×g for 5 min with two subsequent washing steps with 50 ml of acetone and one with 50 ml pure diethylether and spinned down at 3,000×g for 20 min. The precipitate (Imp A) was dried o/n in a vacuum desiccator.

Adenylation of the 5' phosphorylated linker (ordered from Microsynth AG (Balgach, CH), Seq ID: 10) was performed by mixing 200 µM of the oligo with 25 mM MgCl$_2$ and 50.05 mM ImpA and incubating the reaction mixture at 50° C. for 3 h. The preadenylated linker (Seq ID: 11) was PAGE purified afterwards.

Ligation:

The cDNA (Seq ID: 9) of exonuclease digested samples was ligated using a double stranded adaptor of the preadenylated linker (Seq ID: 11) hybridized to a primer with the complementary sequence (Seq ID: 12). Therefore 9.76 pmol of both oligonucleotides were mixed into 40 µl reaction containing 50 mM Tris (pH 7.8), 10 mM MnCl2, 5 mM DTT, 20 U RNasin Ribonuclease Inhibitor (Promega Corporation, Wisconsin, USA), 0.033 U PPase (Fermentas GmbH, St. Leon-Rot, Germany), 20% PEG 8000 and 200 U T4 RNA ligase 2, truncated (New England Biolabs GmbH, Frankfurt am Main, Germany) and incubated at 25° C. for 3 h. After EtOH precipitation the samples were mixed with 100% formamide loading buffer, denatured at 95° C. for 2 min, cooled on ice and resolved by electrophoresis in a 15% acrylamide/7M urea gel. Ligation will result in a 82 nt desired ligation product (Seq ID: 13) and a background ligation of the linker to the free 3' OH of the RNA yielding a 59 or 60 nt fragment (Seq ID: 14, Seq ID: 30-32).

Figure 4A:
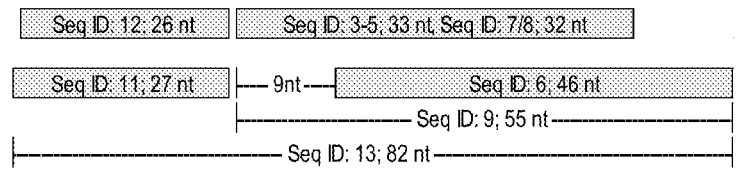
Figure 4B:
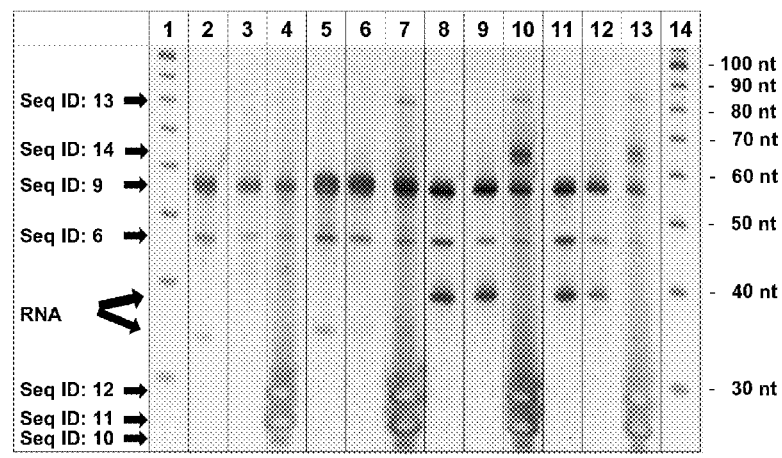

For Lambda Exonuclease results are shown in FIG. 4b. In the different lanes the RNA (Seq ID: 3-5, 7, 8) for reverse transcription, exonuclease digestion and ligation was varied, having different 5' ends. RNA with monophosphate (Seq ID: 7) is in lane 2-4, OH (Seq ID: 8) in lane 5-7, c0 cap (Seq ID: 4) in lane 8-10 and c1 cap (Seq ID: 5) in lane 11-13. The samples after reverse transcription are depicted in lane 2, 5, 8, 11 showing a 55 nt long cDNA (+1-3 nt added due to the terminal transferase activity of M-MLV). Samples after exonuclease digestion are presented in lane 3, 6, 9, 12 and after ligation in lane 4, 7, 10, 13 with the respective RNAs. Lane 1 and 14 show 100 ng of a size marker (10 by DNA ladder, Life Technologies Corporation, New York, USA).

Depending on the 5' end of the RNA (P/OH/cap) the amount of non-templated nucleotide addition to the 3' end of the cDNA differs. While for RNAs with 5' OH/P 1-3 nt are added, it is to about 95% just 1 nt for the cap structure (c0/c1), being accessible for ligation.

It can be seen that RNA with a 5' monophosphate gets digested after the digestion step with Lambda Exonuclease (lane 3) while all other RNAs (5' OH, c0, c1) are protected and remain in the reactions, resulting in the desired ligation product at 82 nts (Seq ID: 13) but also a background reaction product is present (59 nt or 60 nt; Seq ID: 14, 30, 31) that runs at 62-63 nt, showing the ligation of the 3' end of the RNA to the linker (Seq ID: 11). This ligation will not take place with mRNA when the RT-primer primes the poly A tail internally, thus the 3' end of the RNA will not be in a double strand conformation with the primer and no double strand specific ligation can take place.

Figure 4C:
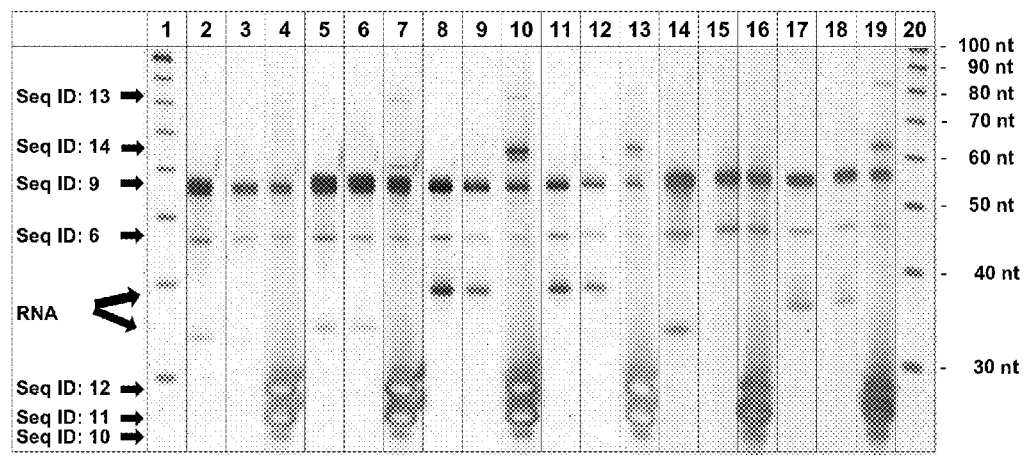

For XRN-1 results are shown in FIG. 4c:

See above description of FIG. 4a, including 5' OH RNA (Seq ID: 8) that was phosphorylated with Optikinase (from Affymetrix California, USA, 1 U/µl) in lane 14-16 and triphosphate (Seq ID: 3) in lane 17-19, wherefore lane 14 and 17 also show the samples after reverse transcription, lane 15 and 18 after exonuclease digestion and lane 16 and 19 after ligation with the respective RNAs. Lane 1 and 20 show 100 ng of a size marker (10 by DNA ladder, Life Technologies Corporation, New York, USA).

RNA with a 5' monophosphate gets digested with XRN-1 (lane 3) while beside RNAs with 5' OH, c0, c1 also 5' 3p are protected from digestion and remain in the reaction, resulting in the desired ligation product (82 nt, Seq ID: 13). The same background reaction as for Lambda Exonuclease is taking place, showing a 59-60 nt product (running at 62-63 nt) (Seq ID: 14, Seq ID: 30-32). Phosphorylation of the RNA with 5' OH with Optikinase makes the RNA also accessible for exonuclease digestion and a double strand specific ligation cannot take place (FIG. 4c, lane 16).

Example 4A: Validation of POC on Capped or Decapped RNA Samples of Natural Source To investigate whether the protocol would be specific for capped mRNA of a natural source an assay was set up comparing capped mRNA to mRNA that was decapped with Tobacco Acid Pyrophosphatase (TAP). TAP treatment results in a 5' monophosphate that renders the RNA molecule sensitive to 5'-3' exonuclease digestion. Therefore the 3' end of cDNA from such decapped mRNA will not be in a hybrid after RT and exonuclease digestion and thus not participate in a double strand specific ligation. In a subsequent qPCR a global cDNA amplification was carried out to record the Ct values. The delta of these Ct values between the mRNA sample (+cap) and the Tap treated mRNA (–cap) will show the sensitivity of the protocol.

TAP Treatment of Total RNA

Tobacco Acid Pyrophosphatase (TAP, from Epicentre Biotechnologies, Wisconsin, USA), (1 U/µl) was used to decap total RNA from mouse liver. The reaction was carried out according to manufacturer and then purified by EtOH precipitation.

cDNA Synthesis:

First-strand cDNA synthesis was carried out using MMLV-H Point Mutant from Promega Corporation (Wisconsin, USA) (200 U/µl). A 5'PTO protected oligo dT primer for cDNA synthesis (Seq ID: 15) was ordered from Sigma-Aldrich Handels GmbH (Missouri, USA). 2 µg total RNA, 50 nM oligo (Seq ID: 15) and 20 U RNasin Ribonuclease Inhibitor (Promega Corporation, Wisconsin, USA) were mixed in a 10 µl volume and denatured at 70° C. for 30 sec with a subsequent decrease in temperature to 41° C. for a 1 min hold. After addition of all other required components including buffer (50 mM Tris-HCl (pH 8.3), 75 mM KCl, 3 mM MgCl$_2$ and 10 mM DTT), 0.5 mM each dNTP and 200 U of reverse transcriptase to a final reaction volume of 20 µl, the reaction was continued for another 2 min at 41° C., followed by a hold at 46° C. for 50 min and then purified by Phenol/Chloroform extraction and EtOH precipitation.

5'-3' Exonuclease Digestion:

The samples were exposed to 5'-3'Exonuclease digestion using XRN-1 from New England Biolabs GmbH (Frankfurt am Main, Germany) (1 U/μl). The reaction mixture of 20 μl contained buffer (50 mM Tris-HCl, 100 mM NaCl, 10 mM MgCl$_2$, 1 mM DTT; (pH 7.9 @ 25° C.)), 20% PEG 8000 and 1 U of enzyme. The reaction was carried out at 37° C. for 60 min and was then purified by Phenol/Chloroform extraction and EtOH precipitation.

Ligation:

The cDNA (with or without previous Exonuclease digestion) was ligated using a double stranded adaptor of the preadenylated linker (Seq ID: 11, see Example 3) hybridized to an oligonucleotide of complementary sequence (Seq ID: 12).

For a 40 μl ligation reaction 22.4 pmol of both oligonucleotides (~30% preadenylated, see Example 3, Seq ID: 11) were mixed with all required components including buffer (50 mM Tris (pH 7.8), 10 mM MnCl2, 5 mM DTT), 20 U RNasin Ribonuclease Inhibitor (Promega Corporation, Wisconsin, USA), 0.033 U PPase (Fermentas GmbH, St. Leon-Rot, Germany), 20% PEG 8000 and 200 U T4 RNA ligase 2, truncated (New England Biolabs GmbH, Frankfurt am Main, Germany) (200 U/μl) and incubated at 25° C. for 3 h and then purified by Phenol/Chloroform extraction and EtOH precipitation.

qPCR Amplification:

A real-time PCR was carried in a 20 μl reaction containing 1 μl cDNA (synthesized from 2 μg total RNA, dissolved in 20 μl 10 mM Tris, pH 8.0 after purification), buffer (50 mM Tris-Cl pH 9.2, 16 mM ammonium sulfate, 0.025% Brij 58, and 5.1 mM magnesium chloride), 1.3 M Betaine, 1.3% DMSO, 0.4 mM dNTPs each, 0.3 μM 5' (Seq ID: 16) and 3' (Seq ID: 17) primer, 1.2 U Klen Taq AC (from DNA Polymerase Technology Inc., Missouri, USA, 5 U/μl), 0.3 U Pfu (from Promega Corporation, Wisconsin, USA, 3 U/μl) and 0.1× SYBRGreen I. Samples were denatured at 95.8° C. for 15 sec, and cycled 42 times at 95.8° C. for 15 sec, 55° C. for 30 sec, 74° C. for 20 min. PCR products were silica purified using silica column (Binding buffer=20% (v/v) Gu-HCl/80% (v/v) EtOH, Wash Buffer=20% (v/v) 100 mM Tris, 400 mM NaCl pH 7.5/80% (v/v) EtOH), eluted in 20 μl 10 mM Tris pH 8.0 and 3 μl were loaded onto a 0.7% agarose gel.

Results are shown in FIG. 5A. Lane 2 shows the amplification of the cDNA synthesized of total RNA without Exonuclease treatment, while the same RNA after XRN-1 digestion is presented in lane 3. In lane 4 and 5 TAP treated RNA was used, without (lane 4) or with digestion (lane 5). 100 ng of GeneRuler™ 1 kb Plus DNA Ladder from Fermentas GmbH (St. Leon-Rot, Germany) are shown in lane 1 and 6. The corresponding Ct-values are 22.44 (lane 2), 23.84 (lane 3), 22.82 (lane 4) and 26.76 (lane 5). It can be seen that the decapped RNA with 5' monophosphate results in a reduced banding pattern and higher ct-values after being digested with XRN-1, compared to not TAP treated RNA.

Example 4B: Validation that an Adapter with a 5' Overhang Ligates to a cDNA::Capped RNA Hybrid Generated by Reverse Transcription of mRNA As shown in example 2A an adapter with a 5' overhang will ligate to a capped RNA::cDNA hybrid, when the cap is provided as an overhang. However, when the capped RNA::cDNA hybrid is created by reverse transcription of capped RNA, this cap overhang will only be present, when the RT stops after reverse transcribing the nucleotide before the cap and not adding any further nucleotide or nucleotides. As prior art [9, e.g.: FIG. 2, lane 1] teaches that MMLV-RT (-H) adds preferably 1 C when it reaches the cap, it was not clear if sufficient cap overhangs would be present after reverse transcription. However, on the other hand the current inventors found that this cap dependent C addition can be reduced by e.g. decreasing dNTP concentration (e.g. 0.1 mM each dNTP) providing for increased cap overhangs.

Therefore it was investigated if under such favorable reverse transcription conditions, a capped RNA::cDNA hybrid can be generated that has a cap overhang and can be ligated to an adapter with a 5' overhang as shown in example 2A, yielding results as in Example 4A.

cDNA Synthesis:

First-strand cDNA synthesis was carried out using MMLV-H Point Mutant from Promega Corporation (Wisconsin, USA) (200 U/μl). A 5'PTO protected oligo dT primer for cDNA synthesis (Seq ID: 43) was ordered from Sigma-Aldrich Handels GmbH (Missouri, USA). 2 μg total RNA from mouse liver, 50 nM oligo (Seq ID: 43) and 20 U RNasin Ribonuclease Inhibitor (Promega Corporation, Wisconsin, USA) were mixed in a 10 μl volume and denatured at 70° C. for 30 sec with a subsequent decrease in temperature to 37° C. for a 1 min hold. After addition of all other required components including buffer (50 mM Tris-HCl (pH 8.3), 75 mM KCl, 3 mM MgCl$_2$ and 10 mM DTT), 0.1 mM each dNTP and 200 U of reverse transcriptase to a final reaction volume of 20 μl, the reaction was continued for another 2 min at 37° C. and followed by a hold at 46° C. for 50 min The sample was purified using silica column (Binding buffer=20% (v/v) Gu-HCl/80% (v/v) EtOH, Wash Buffer=20% (v/v) 100 mM Tris, 400 mM NaCl pH 7.0/80% (v/v) EtOH) and eluted in 20 μl 10 mM Tris pH 8.0.

Ligation:

The cDNA was ligated using a double stranded adaptor of the preadenylated linker (Seq ID: 34, for preadenylation see Example 3) hybridized to an oligonucleotide of complementary sequence (Seq ID: 35).

For a 20 μl ligation reaction 4 pmol of both oligonucleotides (~30% preadenylated) were mixed with all required components including buffer (50 mM Tris (pH 7.8), 10 mM MgCl2, 1 mM ATP, 10 mM DTT), 20 U RNasin Ribonuclease Inhibitor (Promega Corporation, Wisconsin, USA), 0.033 U PPase (Fermentas GmbH, St. Leon-Rot, Germany), 20% PEG 8000 and 400 U T4 DNA ligase (New England Biolabs GmbH, Frankfurt am Main, Germany)(200 U/μl), incubated at 25° C. for 3 h and then purified using a silica well plate (Binding buffer=20% (v/v) Gu-HCl/80% (v/v) EtOH, Wash Buffer=20% (v/v) 100 mM Tris, 400 mM NaCl pH 7.5/80% (v/v) EtOH, elution buffer=10 mM Tris pH 8.0).

qPCR Amplification:

A real-time PCR was carried in a 20 μl reaction containing 1 μl cDNA (synthesized from 2 μg total RNA, dissolved in 20 μl 10 mM Tris, pH 8.0 after purification), buffer (50 mM Tris-Cl pH 9.2, 16 mM ammonium sulfate, 0.025% Brij 58, and 5.1 mM magnesium chloride), 1.3 M Betaine, 1.3% DMSO, 0.4 mM dNTPs each, 0.3 μM 5' (Seq ID: 45) and 3' (Seq ID: 44) primer, 1.2 U Klen Taq AC (from DNA Polymerase Technology Inc., Missouri, USA, 5 U/μl), 0.3 U Pfu (from Promega Corporation, Wisconsin, USA, 3 U/μl) and 0.1× SYBRGreen I. Samples were denatured at 95.8° C. for 15 sec, and cycled 16 times at 95.8° C. for 15 sec, 55° C. for 30 sec, 74° C. for 20 min. PCR products were silica purified using silica column (Binding buffer=20% (v/v) Gu-HCl/80% (v/v) EtOH, Wash Buffer=20% (v/v) 100 mM Tris, 400 mM NaCl pH 7.5/80% (v/v) EtOH), eluted in 20 µl 10 mM Tris pH 8.0 and 3 µl were loaded onto a 0.7% agarose gel.

Results are shown in FIG. 5B. Lane 2 shows the amplification of the cDNA synthesized of total RNA. 100 ng of GeneRuler™ 1 kb Plus DNA Ladder from Fermentas GmbH (St. Leon-Rot, Germany) are shown in lane 1. It can be seen that the natural RNA input yields a banding pattern ranging from 400 to >5000 bp.

Example 5A: Validation of POC on Total RNA Samples Comparing 3' Tagging of cDNA from mRNA or rRNA Ribosomal RNAs (rRNA) are the main species in a sample of total RNA. However as rRNA has a 5' phosphate the 5'-3' exonuclease digestion step of the current invention should deplete the rRNA in rRNA::cDNA hybrids and thus not label the 3' ends of these cDNA molecules in the double strand specific ligation step. Thus an assay similar to Example 4 was set up to test this hypothesis. A random primer was used to prime mRNA as well as rRNA during RT. In principal the reaction flow is as depicted in FIG. 1. A qPCR assay was carried out using a gene specific primer for mRNA (actin (act) and beta 2 microglobolin (b2m)) as well as rRNA (18S rRNA) together with a primer hybridizing to the linker sequence added during the ligation reaction.

When comparing the delta of the Cts of +/− exonuclease reactions, the delta should be higher for rRNA compared to mRNA. In the example two different 5'-3' specific exonucleases where used, XRN-1 (Δct=3.83) and lambda exonuclease (Δct=6.07).

cDNA Synthesis:

First-strand cDNA synthesis was carried out on total RNA (extracted from mouse liver) using MMLV-H Point Mutant from Promega Corporation (Wisconsin, USA, 200 U/µl). A random nonamer primer with a 5'PTO protected overhang for cDNA synthesis (Seq ID: 18) was ordered from Sigma-Aldrich Handels GmbH (Missouri, USA). 2 µg total RNA, 2.5 µM oligo (Seq ID: 18) and 20 U RNasin Ribonuclease Inhibitor (Promega Corporation, Wisconsin, USA) were mixed in a 10 µl volume and denatured at 70° C. for 30 sec and put on ice. After addition of all other required components including buffer (50 mM Tris-HCl (pH 8.3), 75 mM KCl, 3 mM MgCl$_2$ and 10 mM DTT), 0.5 mM each dNTP and 200 U of reverse transcriptase to a final reaction volume of 20 µl, the reaction was started at 4° C. with a slowly increase in temperature (ramp speed of 5% on an ABI9700 thermal cycler) to 46° C. with a hold at 20° C. for 1 min in between. The reaction was hold at 46° C. for 50 min and then purified by phenol/chloroform extraction and EtOH precipitation.

Samples that underwent XRN-1 exonuclease digestion: The sample was exposed to XRN-1 from New England Biolabs GmbH (Frankfurt am Main, Germany) (1 U/µl). The reaction mixture (30 µl) contained buffer (50 mM Tris-HCl, 100 mM NaCl, 10 mM MgCl$_2$, 1 mM DTT, pH 7.9 at 25° C.), 20% PEG 8000 and 3 U of enzyme. The reaction was carried out at 37° C. for 60 min and was Phenol/Chloroform purified afterwards.

Samples that underwent Lambda exonuclease digestion: The sample was exposed to Lambda exonuclease from New England Biolabs GmbH (Frankfurt am Main, Germany) (5 U/µl). The reaction mixture (30 µl) included buffer (67 mM Glycine-KOH, 2.5 mM MgCl$_2$, 50 µg/ml BSA, pH 9.4 at 25° C.), 20% PEG 8000 and 15 U of Lambda Exonuclease. The reaction was carried out at 37° C. for 60 min and purified by Phenol/Chloroform extraction and EtOH precipitation.

Ligation was carried out as described in Example 4.

Gene-Specific qPCR:

A qPCR was carried out in a 20 µl reaction containing 1 µl cDNA (synthesized from 2 µg total RNA, dissolved in 20 µl 10 mM Tris, pH 8.0 after purification), buffer (50 mM Tris-Cl pH 9.2, 16 mM ammonium sulfate, 0.025% Brij 58, and 5.1 mM magnesium chloride), 1.3 M Betaine, 1.3% DMSO, 0.4 mM dNTPs each, 0.3 µM linker specific 5' primer (Seq ID: 16), 0.3 µM gene-specific 3' primer (Seq ID: 19 for 18 S, Seq ID: 20 for act, Seq ID: 21 for b2m), 1.2 U Klen Taq AC (from DNA Polymerase Technology Inc., Missouri, USA, 5 U/µl), 0.3 U Pfu (from Promega Corporation, Wisconsin, USA, 3 U/µl) and 1× SYBRGreen I. Samples were denatured at 95.8° C. for 15 sec, and cycled 50 times at 95.8° C. for 15 sec, 55° C. for 30 sec, 74° C. for 30 sec.

Results:

For each exonuclease a separate experiment was carried out. Results of both experiments are shown in Table 1.

TABLE 1

Results of a qPCR assay comparing Ct values of +/− exo-nuclease reactions between actin and beta 2 microglobulin on the one side and 18S rRNA on the other side.

| | ct-value 18 S | Δct +/− Exo | ct-value act | Δct +/− Exo | ct-value b2m | Δct +/− Exo |
|---|---|---|---|---|---|---|
| XRN-1 | | | | | | |
| − | 23.9 | 3.83 | 35.36 | −1.45 | 27.26 | 1.21 |
| + | 27.73 | | 33.91 | | 28.47 | |
| Lambda | | | | | | |
| − | 22.14 | 6.07 | 33.35 | 1.48 | 35.64 | 0.54 |
| + | 28.21 | | 34.83 | | 36.18 | |

The delta Ct (+/− exonuclease) for the 18S rRNA is 3.83 for the XRN-1 samples and 6.07 for the lambda exonuclease samples, showing that the exonucleases deplete the 18S rRNA in the RNA::cDNA hybrid. In contrast, the delta Ct average (+/− exonuclease) for the two genes is 0.015 in case of XRN-1 and 0.875 for the lambda exonuclease, showing that the mRNA is largely protected from digestion. However, it cannot be excluded that the positive delta Ct for the mRNAs is actually due to a slight degradation of the mRNA. This is totally consistent with one of the aims of the current invention, to only label the cDNA from mRNAs whose 5' cap is present. These results indicate that the mRNA specific cDNA was enriched on average about 14 fold for XRN-1 and about 62 fold for lambda exonuclease.

Example 5B: Gene-Specific qPCR Assay Using Total RNA+/−TAP Treatment to Verify Cap Specificity of the 5' Overhang Adapter Ligation Used in Example 4B Cap specificity of the ligation was evaluated using total RNA from mouse liver that was either TAP treated (+TAP) or not (TAP). Tobacco acid pyrophosphatase (TAP) removes the cap structure of mRNAs, leaving a 5'P end on the RNA. Here, beta-2-microglobulin mRNA was used as reference mRNA originally harboring a 5' cap structure, whereas 18S ribosomal RNA (18S rRNA) was used as a control with a native 5'P end.

Assay:

Total RNA with or without TAP treatment was reverse transcribed as described in Example 5A, but with 0.1 mM of each dNTP. Cap-dependent linker ligation was as in Example 1B, and the PCR assay was performed as in Example 5A but with primers listed in Table 2. Internal primers do not target the 5' tagging sequence but are gene-specific, whereas 5'-specific amplification requires both, a 5' tag- and a gene-specific primer binding site.

Results:

The results are shown in Table 2. The sample without TAP treatment shows a Ct value for the 18S rRNA 5'-specific amplicon that is higher than for the corresponding internal amplicon. The ΔCt of 9.8 cycles indicates a lack of 5' tagging, with an almost identical value for the TAP-treated sample (ΔCt of 9.12). The beta-2-microglobulin 5'-specific and the b2m internal amplicons, however, show highly similar Ct values (ΔCt of 0.82) in the −TAP sample, implying a highly (>50%) efficient tagging of the reverse transcribed, capped mRNA. TAP treatment significantly reduces this tagging, as indicated by the higher Ct for the 5'-specific amplicon (ΔCt of 6.56 cycles). Together, these results show that a 5' tag can be ligated specifically to cDNAs of capped mRNAs.

TABLE 2

Results of a qPCR assay investigating the cap-specific 5' tagging of beta-2-microglobulin mRNA in comparison to 18S ri-bosomal RNA in total RNA samples +/− TAP treatment.

| Amplicons | Primers | −TAP: Ct | +TAP: Ct |
|---|---|---|---|
| 18S 5' | Seq ID: 16 & 19 | 20.92 | 21.05 |
| 18S internal | Seq ID: 19 & 46 | 11.12 | 11.93 |
| B2m 5' | Seq ID: 16 & 21 | 18.92 | 25.39 |
| B2m internal | Seq ID: 47 & 48 | 18.10 | 18.83 |

Example 6: Sanger Sequencing to Determine the Junction Between Linker and cDNA

As in the artificial assay of Example 1 both cDNAs with or without a nucleotide for the cap was ligated, and it was not clear how the sequence at the junction between the linker and the 3' end of the cDNA would look like after RT and ligation in an RNA sample of natural source, an experiment was carried out to determine that using a sample of total RNA.

cDNA synthesis was done as in Example 5.

XRN-1 Exonuclease Digestion:

The cDNA was exposed to XRN-1 from New England Biolabs GmbH (Frankfurt am Main, Germany) (1 U/μl). The reaction mixture (20 μl) contained buffer (50 mM Tris-HCl, 100 mM NaCl, 10 mM $MgCl_2$, 1 mM DTT, pH 7.9 at 25° C.), 20% PEG 8000 and 1 U of enzyme. The reaction was carried out at 37° C. for 60 min and was purified by Phenol/Chloroform extraction and EtOH precipitation.

Lambda Exonuclease digestion was done as in Example 5.

T7 Exonuclease Digestion:

The cDNA was exposed to T7 Exonuclease. The reaction mixture (20 μl) included buffer (20 mM Tris-acetate, 50 mM potassium acetate, 10 mM Magnesium Acetate, 1 mM DTT, pH 7.9 at 25° C.) and 20 U of T7 Exonuclease from New England Biolabs GmbH (Frankfurt am Main, Germany) (10 U/μl). The reaction was carried out at 25° C. for 60 min and purified by Phenol/Chloroform extraction and EtOH precipitation.

Ligation was carried out as in Example 4.

Gene-specific qPCR was carried out as in Example 5 using the linker specific 5' primer (Seq ID: 16) and gene-specific 3' primer (Seq ID: 21 for b2m). 3 μl out of the 20 μl reaction were mixed with 100% formamide loading buffer, denatured at 95° C. for 2 min, cooled on ice and resolved by electrophoresis in a 12% acrylamide/7M urea gel. The desired product band of about 299 nt was cut out and incubated o/n in 0.3 M sodium-acetate, EtOH-precipitated and reamplified for 23 cycles using the same primers and reaction conditions as above. After silica purification using silica column (Binding buffer=20% (v/v) Gu-HCl/80% (v/v) EtOH, Wash Buffer=20% (v/v) 100 mM Tris, 400 mM NaCl pH 7.5/80% (v/v) EtOH), eluted in 20 μl 10 mM Tris pH 8.0) the samples were send for Sanger sequencing by Microsynth AG (Balgach, CH).

Sequencing results all show that an additional nucleotide appears for the cap at the junction (Seq ID: 29) which can consist of any nucleotide, while T>C>A=G is preferred.

REFERENCE LIST

1. Furuichi, Y. and Miura, K. (1975) Nature, 253, 374-375.
2. Maruyama, K. and Sugano, S. (1994) Gene, 138, 171-174.
3. Suzuki, Y. et al. (1997) Gene, 200, 149-156.
4. Invitrogen (2004) GeneRacer Kit—Manual.
5. Carninci, P. et al. (1997) DNA Res, 4, 61-66.
6. Carninci, P. et al. (1996) Genomics, 37, 327-336.
7. Edery, I. et al. (1995) Mol. Cell Biol., 15, 3363-3371.
8. Efimov, V. A. et al. (2001) Nucleic Acids Res, 29, 4751-4759.
9. Schmidt, W. M. and Mueller, M. W. (1999) Nucleic Acids Res., 27, e31.
10. Cloonan, N. et al. (2008) Nat Methods, 5, 613-619.
11. Carninci, P. et al. (1998) Proc. Natl. Acad. Sci. U. S. A, 95, 520-524.
12. Spiess, A. N. and Ivell, R. (2002) Anal. Biochem., 301, 168-174.
13. Lau, N. C. et al. (2001) Science, 294, 858-862.

The invention claimed is:

1. A method for generating a labelled nucleic acid from an RNA comprising a 5' protecting group, said method comprises the steps of:
   a) obtaining a mixture of template strands of nucleic acids, said mixture comprising said RNA comprising a 5' protecting group and further potentially other nucleic acids without a 5' protecting group,
   b1) annealing at least one oligonucleotide primer to said mixture of RNA template strands, and extending said primer in a template sequence dependent manner, thereby obtaining a duplex of a complementary nucleic acid strand annealed to its template strand of said RNA comprising a 5' protecting group and a duplex of a complementary nucleic acid strand annealed to said potentially present other nucleic acid without a 5' protecting group, or b2) providing the RNA and potentially further other nucleic acids in duplex with a complementary nucleic acid strand annealed to its template strand, thereby providing a duplex of said nucleic acids comprising a 5' protecting group and potentially a duplex of said nucleic acids without a 5' protecting group, and
   performing either steps c) and d1); or step d2), wherein
   c) comprises modifying the duplex of said nucleic acids without a 5' protecting group either on the 5' end of the template strand or on the 3' end of the complementary strand, or both; wherein
   d1) comprises labelling a complementary nucleic acid of a double stranded nucleic acid not modified in step c); and wherein
   d2) comprises labelling a complementary nucleic acid of a double strand obtained or provided in step b1) or b2), wherein said labelling is dependent on the presence of the 5' protecting group on the RNA template strand annealed to said complementary strand by double strand dependent ligation, thereby specifically generating a labelled nucleic acid complementary to an RNA at least originally comprising a 5' protecting group,
   wherein said labeling d1) or d2) is specific for double strands where the 5' protecting group of the RNA strand is present as an overhang at the RNA strand 5' end,
   wherein the 5' protecting group is a protecting group that protects against digestion by 5'-3' exonucleases.

2. The method of claim 1, wherein said labelling of d1) comprises ligating a nucleic acid sequence tag to said double stranded nucleic acid not modified in step c).

3. The method of claim 2, wherein said nucleic acid sequence tag is hybridized with another nucleic acid to form at least partially a double stranded at the ligation end.

4. The method of claim 1, wherein said modification prevents labelling of said modified double strand.

5. The method of claim 1, wherein said modification in step c) is selected from i) 5'-3' exonuclease digestion of uncapped nucleic acids; ii) ligating the 5' end of the template strand without a 5' protecting group to the 3' end of the complementary strand; iii) adding a nucleic acid sequence tag for the unmodified double stranded nucleic acids; or iv) removing 5' terminal phosphates on the template strand.

6. The method of claim 5, wherein the terminal phosphates on the template strand are removed by phosphatase while the RNA still contains the 5' protecting group and is thereby protected from 5' dephosphorylation.

7. The method of claim 1, wherein the complementary nucleic acid of an unmodified double stranded nucleic acids is labelled in step d1) on the 3' end.

8. The method of claim 7, wherein the 3' terminal nucleic acid of the complementary strand is annealed to the template strand with the 5' terminal nucleotide or the protecting group, within 0 or 1 nucleotides of said 5' terminal nucleotide or the 5' protecting group.

9. The method of claim 8, wherein the protecting group is a 5' cap nucleotide.

10. The method of claim 8, wherein the 5' terminal nucleotide is a 5' polyphosphate.

11. The method of claim 1, wherein double strands of the duplex of the nucleic acids comprising a 5' protecting group of either (b1) or (b2) are double strands with at most 1 nucleotide overhangs.

12. The method of claim 1, wherein in step d2) a label, being a double stranded adapter nucleic acid provided with a 5' nucleotide overhang, is ligated to said complementary nucleic acid.

13. The method of claim 12, wherein the ligation is with a double strand specific ligase.

14. The method of claim 12, wherein the 5' nucleotide overhang in the adapter consists of a single nucleotide.

15. The method of claim 1, further comprising the step e) of enriching, selecting, isolating or purifying nucleic acids with the label.

16. The method of claim 15, wherein the purifying is through solid phase binding.

17. The method of claim 1, wherein in step b1) a reverse transcriptase enzyme is used that has inhibited terminal transferase activity or conditions are used that cause a reduction in terminal transferase activity, wherein said reduced activity is as compared to a nonmodified reverse transcriptase at at least 3 mM $Mg^{2+}$ with abundant dNTPs.

18. The method of claim 1, wherein a 3' overhang on the complementary nucleic acid strand if present is digested prior to step d1) or d2).

19. The method of claim 1, wherein in step b1) a reverse transcriptase enzyme that is modified is used, wherein said modification of the enzyme reduces or inhibits the RNAse H activity of the reverse transcriptase enzyme.

20. The method of claim 1, wherein at least one oligonucleotide primer of step b1) is resistant to 5'-3' exonuclease digestion or has a 5' overhang when annealed to the RNA template and wherein said overhang is formed by nucleotides of the oligonucleotide primer that are not bound to the RNA template.

21. The method of claim 1, wherein a nucleic acid sequence tag is used as label and said nucleic acid sequence tag is protected from nuclease digestion.

22. The method of claim 1, wherein on a nucleic acid of step b1) or b2) either a 5' OH is phosphorylated or a 5' phosphate is dephosphorylated.

23. The method of claim 22, wherein either on a nucleic acid of step b1) or b2) a 5' OH is phosphorylated and a 5' phosphate dependent 5'-3' exonuclease is used for modification in step c); or on a nucleic acid of step b1) or b2) a 5' phosphate is dephosphorylated when a 5' OH dependent 5'-3' exonuclease is used for modification in step c).

24. The method of claim 1, wherein step c) is 5'-3' exonuclease modification in the presence of a crowding agent.

25. The method of claim 1, wherein the label comprises a fluorescent molecule.

26. The method of claim 25, wherein the label is a fluorescent nucleic acid sequence tag, or wherein the label provides protection from 3'-5' exonucleolytic digestion.

27. The method of claim 1, wherein the label is immobilized on a solid phase.

28. The method of claim 1, wherein said protecting group is a 5' cap or a 5' polyphosphate.

29. The method of claim 28, wherein the 5' polyphosphate is a 5' triphosphate.

30. The method of claim 1, wherein the labelled nucleic acid is amplified through template dependent nucleotide polymerization with the complementary nucleic acid being the template.

31. The method of claim 1, wherein said 5' protecting group is removed after performing step c).

32. The method of claim 1, wherein said double strands of the duplex of the nucleic acids without a 5' protecting group of either b1 or b2 are double strands with blunt ends or ends with at most 1 nucleotide overhangs.

* * * * *